(12) United States Patent
Purdy et al.

(10) Patent No.: US 7,150,737 B2
(45) Date of Patent: Dec. 19, 2006

(54) METHODS AND APPARATUSES FOR NAVIGATING THE SUBARACHNOID SPACE

(75) Inventors: Phillip D. Purdy, Dallas, TX (US); Ajit Nair, Fremont, CA (US); Kamal Ramzipoor, Fremont, CA (US); Mehran Bashiri, San Carlos, CA (US); Pete Phong Pham, Fremont, CA (US)

(73) Assignees: Sci/Med Life Systems, Inc., Maple Grove, MN (US); Board of Regents, The University of Texas System, Austin, TX (US)

( * ) Notice: Subject to any disclaimer, the term of this patent is extended or adjusted under 35 U.S.C. 154(b) by 395 days.

(21) Appl. No.: 10/328,560

(22) Filed: Dec. 23, 2002

(65) Prior Publication Data

US 2003/0097082 A1 May 22, 2003

Related U.S. Application Data

(63) Continuation-in-part of application No. 09/905,670, filed on Jul. 13, 2001.

(51) Int. Cl.
*A61M 31/00* (2006.01)

(52) U.S. Cl. .................. 604/506; 604/93.01

(58) Field of Classification Search ............. 604/500, 604/506, 508, 510, 522, 39, 93.01, 96.01, 604/113, 117, 151, 152, 153, 264, 272, 523; 128/898
See application file for complete search history.

(56) References Cited

U.S. PATENT DOCUMENTS

| 3,782,388 | A | | 1/1974 | Page |
| 4,335,835 | A | * | 6/1982 | Beigler et al. ............. 222/95 |
| 4,619,643 | A | | 10/1986 | Bai |
| 4,737,146 | A | | 4/1988 | Amaki et al. |
| 4,808,157 | A | | 2/1989 | Coombs |
| 4,838,878 | A | | 6/1989 | Kalt et al. |
| 4,904,237 | A | | 2/1990 | Janese |
| 4,911,163 | A | | 3/1990 | Fina |
| 4,950,232 | A | | 8/1990 | Ruzicka et al. |
| 4,973,305 | A | | 11/1990 | Goltzer |
| 5,085,631 | A | | 2/1992 | Leighton |
| 5,098,393 | A | | 3/1992 | Amplatz et al. |

(Continued)

FOREIGN PATENT DOCUMENTS

DE 37 26 453 2/1989

(Continued)

OTHER PUBLICATIONS

Amar et al., "Microcatheterization of the cervical epidural space via lumbar puncture: Technical note," *Neurosurgery*, 48(5):1183-1187, 2001. Article from the Neurosurgery website at: http://www.neurosurgery-online.com, Oct. 23, 2001.

(Continued)

*Primary Examiner*—Kevin C. Sirmons
*Assistant Examiner*—Mark K Han
(74) *Attorney, Agent, or Firm*—Crompton, Seager & Tufte, LLC

(57) ABSTRACT

Disclosed are methods and devices for navigating a subarachnoid space in a vertebrate organism including percutaneously introducing a device into the spinal subarachnoid space at an entry location. Navigation of the spinal subarachnoid space is disclosed for the purpose of reaching a desired location in the subarachnoid space or the intracranial space, including areas in and around the spinal cord and brain. Once a desired location is reached, methods and devices for cooling or heating the desired location to cause physiologic changes are suggested.

62 Claims, 20 Drawing Sheets

U.S. PATENT DOCUMENTS

| | | | |
|---|---|---|---|
| 5,160,323 A | 11/1992 | Andrew | |
| 5,256,146 A | 10/1993 | Ensminger et al. | |
| 5,297,564 A | 3/1994 | Love | |
| 5,378,241 A | 1/1995 | Haindl | |
| 5,385,152 A | 1/1995 | Abele et al. | |
| 5,397,305 A | 3/1995 | Kawula et al. | |
| 5,423,760 A | 6/1995 | Yoon | |
| 5,423,849 A | 6/1995 | Engelson et al. | |
| 5,445,625 A | 8/1995 | Voda | |
| 5,449,343 A | 9/1995 | Samson et al. | |
| 5,470,318 A | 11/1995 | Griffith, III et al. | |
| 5,478,331 A | 12/1995 | Heflin et al. | |
| 5,520,647 A | 5/1996 | Solar | |
| 5,542,936 A | 8/1996 | Razi | |
| 5,613,950 A | 3/1997 | Yoon | |
| 5,630,802 A | 5/1997 | Moellmann et al. | |
| 5,637,098 A | 6/1997 | Bierman | |
| 5,693,020 A * | 12/1997 | Rauh | 604/151 |
| 5,704,915 A | 1/1998 | Melsky et al. | |
| 5,731,284 A | 3/1998 | Williams | |
| 5,738,650 A | 4/1998 | Gregg | |
| 5,810,869 A | 9/1998 | Kaplan et al. | |
| 5,814,016 A | 9/1998 | Valley et al. | |
| 5,830,188 A | 11/1998 | Abouleish | |
| 5,833,632 A | 11/1998 | Jacobsen et al. | |
| 5,846,226 A | 12/1998 | Urmey | |
| 5,908,385 A | 6/1999 | Chechelski et al. | |
| 5,928,155 A | 7/1999 | Eggers et al. | |
| 5,928,260 A | 7/1999 | Chin et al. | |
| 5,931,810 A | 8/1999 | Grabek | |
| 5,935,122 A | 8/1999 | Fourkas et al. | |
| 5,951,520 A | 9/1999 | Burzynski et al. | |
| 5,980,480 A | 11/1999 | Rubenstein et al. | |
| 5,980,484 A | 11/1999 | Ressemann et al. | |
| 5,980,504 A | 11/1999 | Sharkey et al. | |
| 6,004,262 A | 12/1999 | Putz et al. | |
| 6,004,295 A | 12/1999 | Langer et al. | |
| 6,026,316 A | 2/2000 | Kucharczyk et al. | |
| 6,036,654 A | 3/2000 | Quinn et al. | |
| 6,061,587 A | 5/2000 | Kucharczyk et al. | |
| 6,080,140 A | 6/2000 | Swaminathan et al. | |
| 6,086,548 A | 7/2000 | Chaisson et al. | |
| 6,090,072 A | 7/2000 | Kratoska et al. | |
| 6,120,499 A | 9/2000 | Dickens et al. | |
| 6,129,713 A | 10/2000 | Mangosong et al. | |
| 6,146,354 A | 11/2000 | Beil | |
| 6,162,170 A | 12/2000 | Foley et al. | |
| 6,168,588 B1 | 1/2001 | Wilson | |
| 6,183,443 B1 | 2/2001 | Kratoska et al. | |
| 6,190,349 B1 | 2/2001 | Ash et al. | |
| 6,200,336 B1 | 3/2001 | Pavcnik et al. | |
| 6,214,029 B1 | 4/2001 | Thill et al. | |
| 6,233,488 B1 | 5/2001 | Hess | |
| 6,251,115 B1 | 6/2001 | Williams et al. | |
| 6,272,370 B1 | 8/2001 | Gillies et al. | |
| 6,293,924 B1 | 9/2001 | Bagaoisan et al. | |
| 6,319,241 B1 | 11/2001 | King et al. | |
| 6,328,694 B1 | 12/2001 | Michaeli | |
| 6,352,530 B1 | 3/2002 | Mangosong | |
| 6,379,331 B1 | 4/2002 | Barbut et al. | |
| 6,673,999 B1 | 1/2004 | Wang et al. | |
| 6,699,269 B1 | 3/2004 | Khanna | |
| 2002/0091356 A1 | 7/2002 | Barbut et al. | |

FOREIGN PATENT DOCUMENTS

| | | |
|---|---|---|
| EP | 0 454 264 | 10/1991 |
| EP | 1 062 959 | 12/2000 |
| WO | WO 97/44082 | 11/1997 |
| WO | WO 98/38953 | 9/1998 |
| WO | WO 98/57603 | 12/1998 |
| WO | WO 99/20334 | 4/1999 |
| WO | WO 00/51669 | 9/2000 |
| WO | WO 01/54766 | 8/2001 |
| WO | WO 02/068036 | 9/2002 |

OTHER PUBLICATIONS

Blomberg, "A method for epiduroscopy and spinaloscopy. Presentation of preliminary results," *Acta Anaesthesiol. Scan.*, 29(1):113-116, 1985.

Blomberg, "Fibrous structures in the subarachnoid space: a study with spinalscopy in autopsy subjects," *Anesth. Analg.*, 80(5):875-879, 1995.

Delhaas, "Extradural and subarachnoid catherization using the Seldinger technique," *Br. J. Anaesth.*, 76(1):149-150, 1996.

Eguchi et al., "Endoscopy of spinal cord and posterior fossa by a lumbar percutaneous approach: endoscopic anatomy in cadavers," *Minim. Invasive Neurosurg.* 42(2):74-78, 1999.

Eguchi et al., "Endoscopy of the spinal cord: cadaveric study and clinical experience," *Minim. Invasive Neurosurg.*, 42(3):164-151, 1999.

Fries et al., "Biportal Neuroendoscopic Microsurgical Approaches to the study of Subarachnoid Cisterns, A Cadaver Study," *Minim Invas. Neurosurg.*, 39(4):99-104, 1996.

Hamada et al., "Microcatheter intrathecal urokinase infusion into cisterna magna for prevention of cerebral vasospasm," *Stroke*,31:2141-2148, 2000.

Karakhan et al., "Operative spinal endoscopy: stereotopography and surgical possibilities," *Acta. Neurochir. Suppl.*, 61:108-114, 1994.

Karakhan, "Use of intracranial endoscopy in morphologic studies," *Arkh. Anat. Gistol. Embriol.*, 98(1):75-82, 1990. Russian.

Miyamoto et al., "The development of spinal endoscope using a flexible optic fiber," *No. To. Shinkei*, 41(12):1233-1238, 1989. Abstract on p. 1238.

Stefanov et al., "A new method for transcutaneous coaxial neuroendoscopy," *Anat. Embryol.*, 194(4):319-326, 1996.

Suzukawa et al., "Percutaneous fiberoptic spinal laser endoscopy," *J.Clin Laser Med Surg.*, 8(6):27-30, 1990.

Tanaka et al., "Endoscopic treatment of symptomatic spinal subarachnoid cysts," *AJR Am. J. Roentgenol.*, 169(6):1719-1720, 1997.

Uchiyama et al., "Ultrafine Flexible Spinal Endoscope (Myeloscope) and Discovery of an Unreported Subarachnoid Lesion," *Spine*, 23(21):2358-2362, 1998.

Vinas et al., "Microanatomical basis for the third ventriculostomy," *Minim. Invasive Neurosug.*, 39(4):116-121, 1996.

Document depicting a prototype stent, sent to applicant on Jel. 13, 2001.

"Back Break," Aricle from *Forbes Magazine*, p. 123-124, Aug. 12, 2002.

"Keeping it Cool," Article from *Health Communities, United Hospital*, 11(1):1, 8, Winter 2003.

* cited by examiner

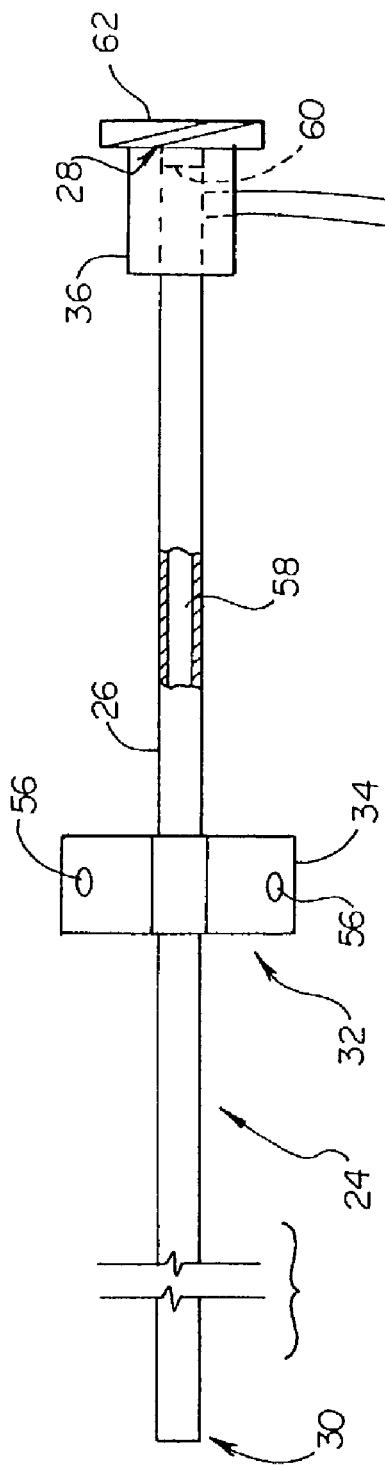
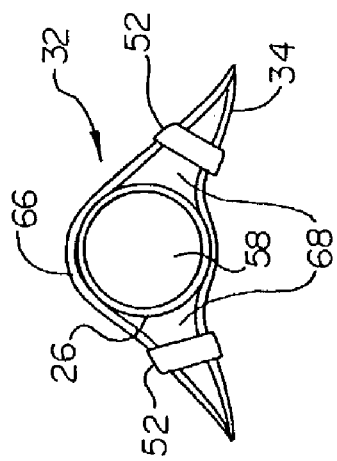
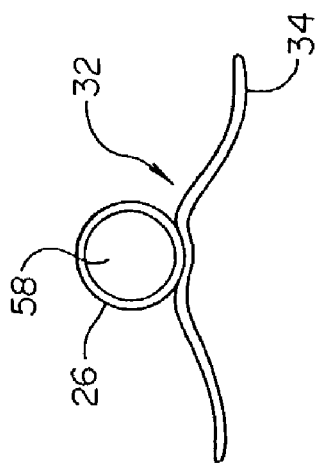
Fig.3
Fig.4
Fig.5

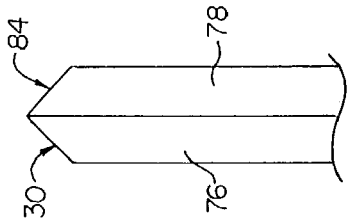
*Fig.13C*
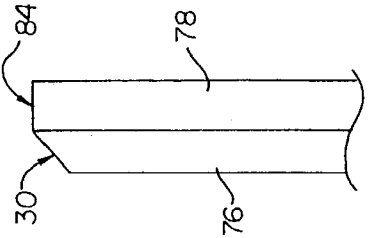
*Fig.13D*
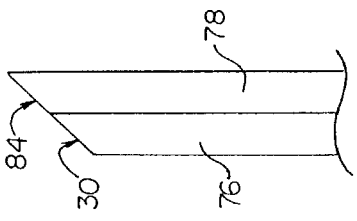
*Fig.13B*
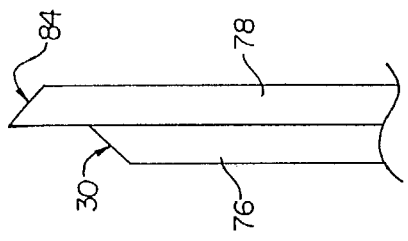
*Fig.13G*
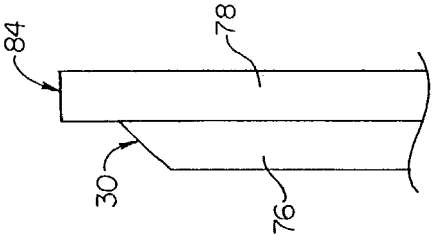
*Fig.13E* *Fig.13F*
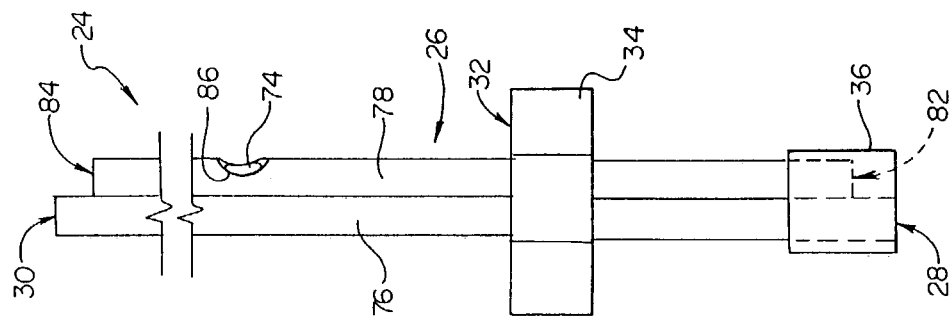
*Fig.13A*

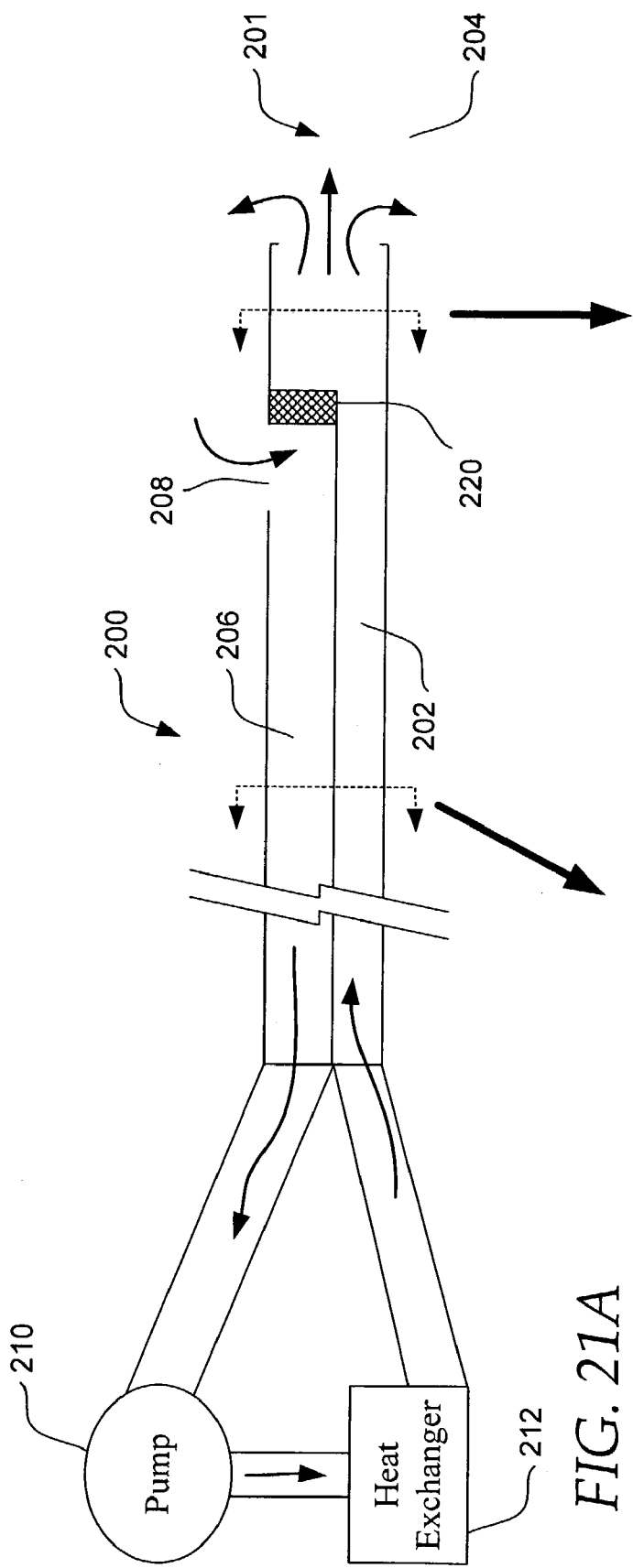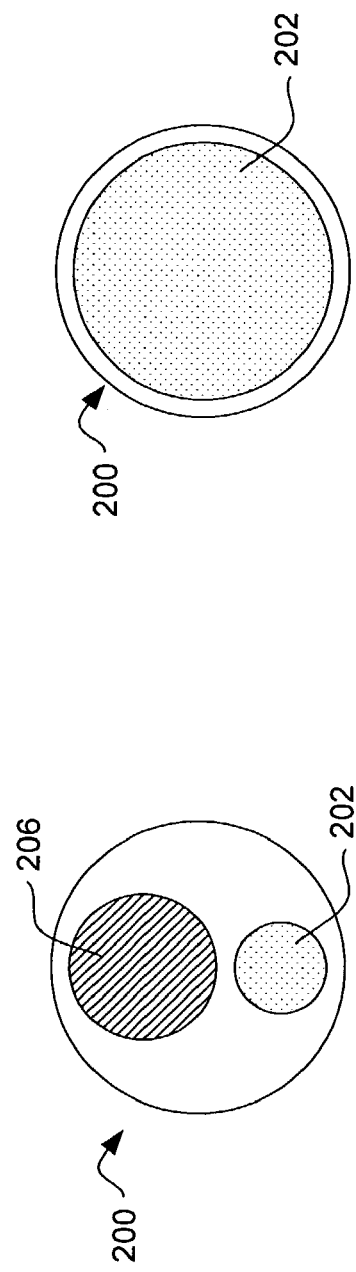
FIG. 21A
FIG. 21B
FIG. 21C

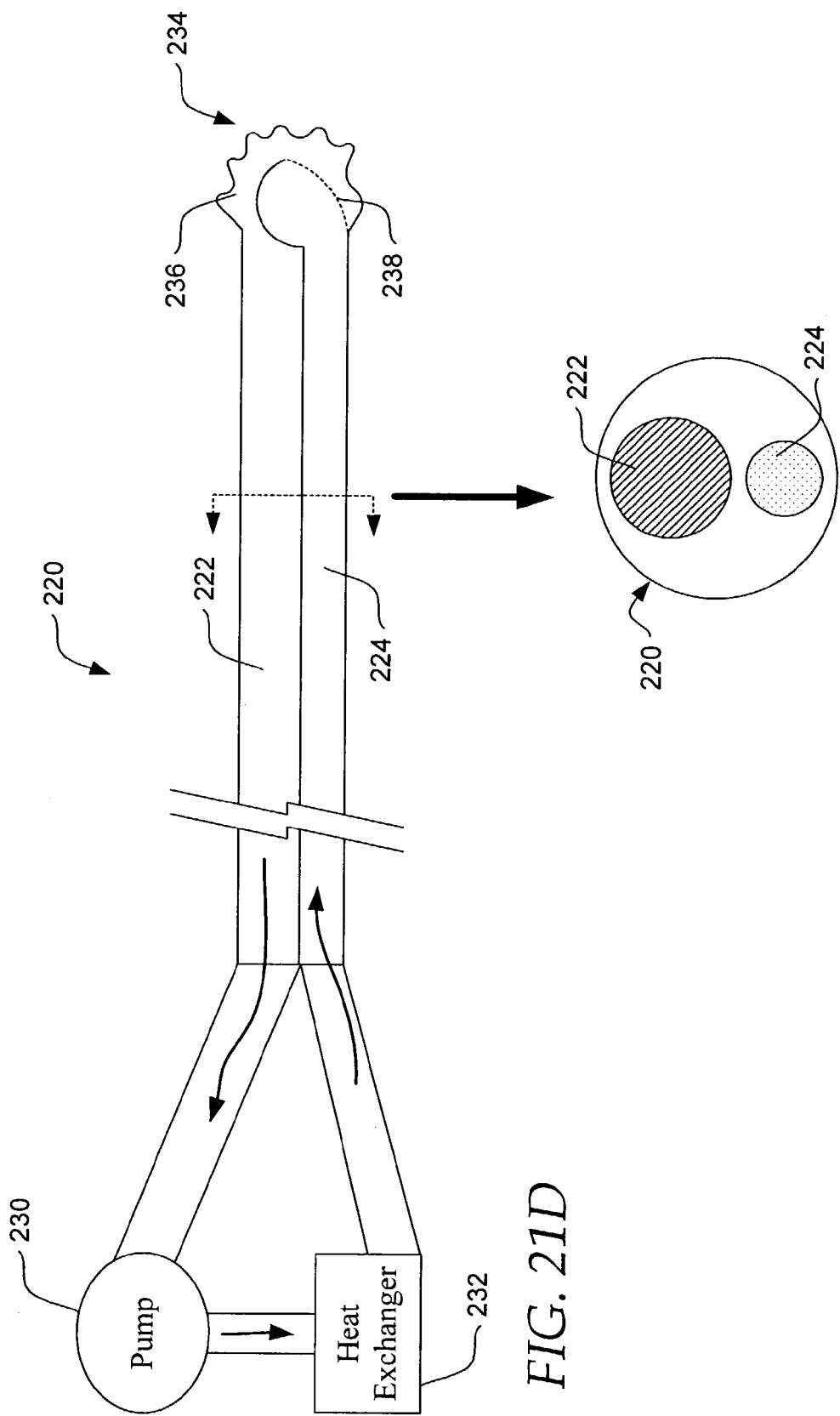

METHODS AND APPARATUSES FOR NAVIGATING THE SUBARACHNOID SPACE

RELATED APPLICATIONS

This is a continuation-in-part of application Ser. No. 09/905,670 filed Jul. 13, 2001 entitled METHODS AND APPARATUSES FOR NAVIGATING THE SUBARACHNOID SPACE, which is incorporated herein by reference.

FIELD OF THE INVENTION

The present invention relates generally to surgical methods and medical devices. More particularly, it concerns methods and apparatuses useful in navigating and performing procedures in the subarachnoid space, including the subarachnoid and intracranial spaces.

BACKGROUND

During the 20th century, brain neurosurgery has advanced via the introduction of microsurgical techniques, the development of new tools such as aneurysm clips, and the description of new operative approaches. Surgeons have developed elegant mechanisms to remove parts of the bones making up the skull (craniotomy) and operate on structures deep within the brain while attempting to minimize complications relating to the approach. The surgical approach to the intracranial and spinal subarachnoid space has historically included skin incision, dissection to either the cranium or spinal bony covering, removal of some bone, and dissection through the meninges to gain access to the neurological structures. While imaging modalities became integrated into diagnostic evaluations, only at the end of the last century were significant attempts made to integrate computed tomography, angiography, and most recently magnetic resonance (MR) scanning into the actual surgical procedures.

Unfortunately, craniotomy has limited the applicability of some present imaging modalities because the surgeon cannot simultaneously stand at the patient's head to operate on the brain via craniotomy, maintain sterility, and scan the brain using a large scanning apparatus that requires the patient to be held within it. There are limits to the ability to conveniently perform such surgery using currently-available imaging devices due to a conflict between the devices for acquiring images and the methods of operating on the brain.

An additional concern is that, while the brain surface is readily accessed via conventional craniotomy, the approach to deeper structures is progressively more difficult. The brain is often retracted after the craniotomy to facilitate access to different areas in and around the brain, and in some cases there is the need to remove brain tissue to gain access. Both retraction and removal create potential problems with maintaining sterility and avoiding direct injury to tissue, as well as the problem of putting tissue back into place without causing injury.

During the last 20 years, the development of endovascular neurosurgery has resulted in the creation of specialized devices for application within arteries. These devices include not only catheters and guidewires, but also embolic materials that can be introduced via catheters, thereby enabling the enhancement of some procedures that are performed via craniotomy following embolization. In some cases, the need for craniotomy has been eliminated. However, access is limited to that achieved from within blood vessels.

SUMMARY

The present invention provides a variety of methods and devices for providing therapeutic and/or diagnostic tools to physicians. Navigation and catheterization of the subarachnoid space are proposed, and devices and methods for doing so are disclosed. The subarachnoid space is a compartment that contains the body of the spinal cord and cerebrospinal fluid (CSF). The CSF is a fluid that fills and surrounds the ventricles and cavities of the brain and the spinal cord, and acts as a lubricant and a mechanical barrier against shock. It is proposed that access to areas of the spinal cord and even the brain (intracranial space) may be gained by accessing the subarachnoid space. The access may include catheterization that may be used for diagnostic and therapeutic purposes. Several embodiments include catheterization by percutaneous introduction of a catheter at a chosen location of the spinal column into the subarachnoid space. Additional embodiments include introduction of a catheter into the intracranial space and among the lobes of the brain after navigation of the subarachnoid space. Some embodiments further call for use of an introducer sheath to secure access to the subarachnoid space and enable easy introduction or replacement of catheters. Once a desired location can be accessed by such catheterization, therapeutic and diagnostic methods and devices are proposed.

In several embodiments, methods and devices for providing a fluid infusion to areas accessed by catheterization of the subarachnoid space are proposed, including areas of the spinal column and the brain. In some embodiments, the fluid infusion may include materials that can assist in visualization of brain lobes, areas in the spinal column, and other features accessible from the subarachnoid space and/or the intracranial space. In other embodiments, the fluid may contain drugs, medicines, antibiotics, and other substances used for therapeutic and/or diagnostic purposes.

In additional embodiments, the fluid infusion may provide a fluid at a different temperature than the ordinary or existing temperature of the CSF or adjacent tissue. In one embodiment, a fluid having a lower temperature than ordinarily occurring in CSF is provided to an area of the brain or spinal column to induce a local hypothermic state. One therapeutic tool that may provide improved conditions for surgeries involves inducing a localized hypothermic condition. It is widely known that drowning victims who are submerged in cold water may undergo miraculous recoveries, regaining most brain functions even though brain tissue was deprived of oxygen for extended periods of time. One reason is that hypothermic conditions reduce cellular metabolic rates, enabling cells that would otherwise die of oxygen starvation to survive. Inducing a localized hypothermic condition could be a useful way to preserve tissue during operations that limit blood supply for a short time. The hypothermic condition could also help preserve a patient who may have suffered catastrophic injury, allowing doctors more time to perform diagnosis and treatment of the injury. In another embodiment, a fluid of a higher temperature than ordinarily existing in the CSF may be infused to accelerate local cellular metabolism, growth, or to facilitate other diagnostic or therapeutic activities. Additional embodiments call for filtering materials out of the CSF by draining fluid from a first location, filtering the CSF, and infusing it into a second location.

For several embodiments, the infused fluid is actually CSF that is drained from some other area of the subarachnoid space. In one embodiment, CSF is drained from a proximal location and displaced to a distal location along the same catheter. In other embodiments, a first catheter is used to drain CSF while a second catheter is used for infusion of the CSF. Additional embodiments use fluids other than CSF for infusion. Another embodiment uses a catheter introduced into the subarachnoid or intracranial space to drain CSF to control pressure in an area of the brain, and may include an implantable device enabling flow of CSF after the catheter is withdrawn.

Certain embodiments include catheters and methods for enabling a heat transfer to occur within the patient, by providing a heat transfer device inside a catheter. In some embodiments, a catheter is introduced to the subarachnoid space, the catheter including a device for displacing fluid within the subarachnoid space. In other embodiments, the fluid displaced by the catheter is removed from the subarachnoid space and then re-infused or replaced by another fluid.

In some embodiments a catheter is introduced into the spinal subarachnoid space including a fluid displacement device disposed in a distal portion of the catheter. The fluid displacement device may include a collapsible member, a rotatable member, or a balloon in various embodiments. In another embodiment, the catheter may include valves for controlling fluid displacement direction. In several embodiments, the catheter has an inner lumen, and the cross sectional area of a section of the lumen is changeable by electrostatic, magnetostatic, elastic or shape-memory actuation, and the actuation provides a driving force for fluid displacement.

BRIEF DESCRIPTION OF THE DRAWINGS

FIG. 3 is a top view of a medical device suited for attachment to the skin and illustrated as a sheath;

FIGS. 4–9 illustrate different embodiments of the skin-attachment apparatus that is coupled to the sheath shown in FIG. 3;

FIG. 13A illustrates sub-elongated members of different lengths;

FIGS. 13B–H are partial side views illustrating different embodiments of ends of two coupled sub-elongated members;

FIG. 21A is a partial side view of an illustrative embodiment of a catheter for removing and infusing a fluid, including diagrammatic representation of a pump and heat exchanger for use with the catheter;

FIGS. 21B and 21C are cross sectional views of portions of the catheter of FIG. 21A;

FIG. 21D is a partial side view of an illustrative embodiment of a closed system for heat exchanging with an area of tissue and fluid;

FIG. 21E is a cross-sectional view of a portion of the catheter of FIG. 21D;

DESCRIPTION OF ILLUSTRATIVE EMBODIMENTS

Figure 1:
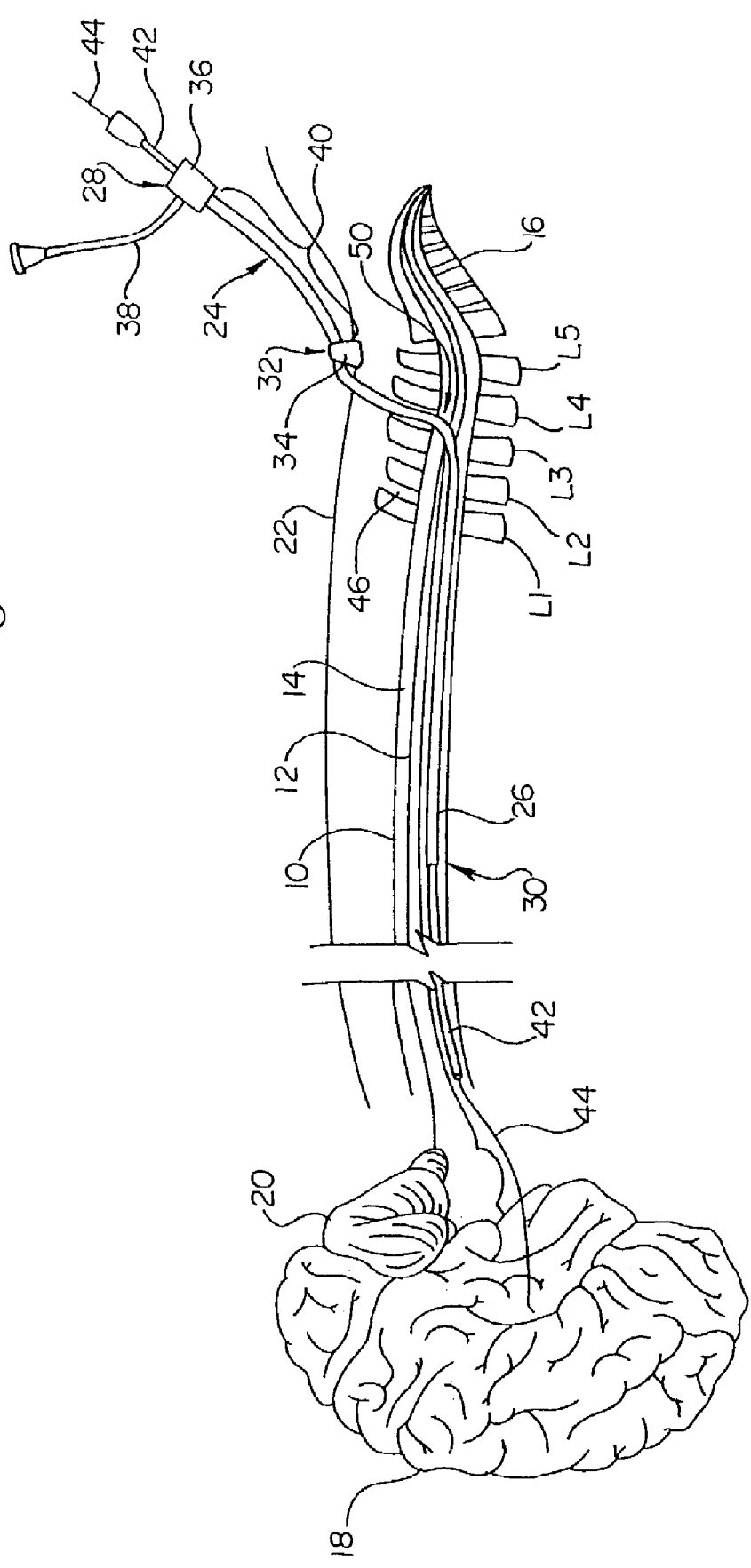
FIG. 1 illustrates selected areas of the central nervous system and medical devices introduced into the spinal subarachnoid space.

The following detailed description should be read with reference to the drawings in which similar elements in different drawings are numbered the same. The drawings, which are not necessarily to scale, depict illustrative embodiments and are not intended to limit the scope of the invention.

As used herein, the term "about" applies to all numeric values, whether or not explicitly indicated. The term "about" generally, refers to a range of numbers that one of skill in the art would consider equivalent to the recited values (i.e. having the same function or result). In many instances the term "about" may include numbers that are rounded to the nearest significant figure.

The present methods involve navigating the subarachnoid space, including the spinal subarachnoid space. In some embodiments, the intracranial space is also navigated. The methods facilitate intracranial access via the subarachnoid space. For example, in some embodiments a first device may be introduced into the subarachnoid space to facilitate intracranial access with another device introduced through one or more passageways located within the first device. In this document, "intracranial access" means access to the space within the head that is above the foramen magnum. In addition, intracranial subarachnoid space is the subarachnoid space located above the foramen magnum, and the spinal subarachnoid space is the subarachnoid space located below the foramen magnum, though the spaces are contiguous.

The present methods offer new routes of access for both brain and spine surgery without requiring craniotomy or bone removal, reducing the invasive nature of such surgeries. The methods may be performed with the operator standing remote from the patient's head. The route of access includes percutaneous introduction of devices into the spinal subarachnoid space, which may in some embodiments be achieved by a standard puncture of the spinal subarachnoid space, for example, in the lumbar, thoracic or cervical regions. Then, techniques conventionally used in other catheterization procedures may be used to navigate the subarachnoid space, as well as, in some embodiments, the intracranial space. Many embodiments of these methods can have fewer problems with exposure of the brain to infectious agents and offer an opportunity for navigation of many structures without brain retraction or removal to achieve access, as compared to techniques using a craniotomy.

While much of the following description includes references to human anatomy, the present invention could be practiced on a variety of other animals. For example, other vertebrate organisms sharing some skeletal similarity to humans may be amenable to methods and devices such as those disclosed herein. One example would be use of methods and devices for introduction into the subarachnoid spaces of animals having a skeletal structure defining such spaces. Thus, for example, in some embodiments the subarachnoid space of other vertebrate organisms including mammals, birds, reptiles, fish or amphibians. Some methods or devices may be useful, for example, in veterinary procedures.

Turning to the figures, FIG. 1 illustrates certain aspects of the central nervous system of a patient that have been navigated using some examples of the present techniques. Specifically, FIG. 1 illustrates dural membrane 10, spinal cord 12, subarachnoid space 14, lumbar vertebrae L1, L2, L3, L4, and L5, sacrum 16, and brain 18, including cerebellum 20. FIG. 1 also illustrates as sheath 24 a medical device suited for attachment to skin 22, which includes elongated member 26, first end 28, second end 30, skin-attachment apparatus 32, valve apparatus 36 coupled to first end 28, and flush line 38. Skin-attachment apparatus 32 includes flexible skin-attachment flap 34 configured for attachment to skin 22. Further, skin-attachment apparatus 32 is configured to be coupled to elongated member 26 at a coupling location along elongated member 26. FIG. 1 illustrates that skin-attachment apparatus 32 and valve apparatus 36, which are both coupled to elongated member 26, define flexible member portion 40 between them.

As shown in FIG. 1, elongated member 26 includes a first passageway that is sized to slidably receive a guidewire, and may be sized large enough to receive other devices including catheters. Elongated member 26 may be advanced a desired distance into the subarachnoid space as shown; in some embodiments the distance is about ten centimeters, though greater and lesser distances may also be chosen. As shown in FIG. 1, another device having a first passageway is illustrated as catheter 42, which has been percutaneously introduced into subarachnoid space 14 at entry location 50 through the first passageway of elongated member 26. Guidewire 44 is shown in FIG. 1 as having been percutaneously introduced into subarachnoid space 14 at entry location 50 through the first passageways of both catheter 42 and elongated member 26.

Prior to percutaneously introducing sheath 24 into subarachnoid space 14 at entry location 50, an operator may direct a guidewire through skin 22 and dural membrane 10 and into spinal subarachnoid space 14 in order to facilitate the introduction of sheath 24. This guidewire introduction may be achieved, for example, by directing a needle through the skin and the dural membrane between any of the lumbar vertebrae. The spaces between adjacent vertebrae are known as interspaces, such as the L1–2 interspace labeled as element 46.

While FIG. 1 illustrates introduction into the subarachnoid space (and specifically into the spinal subarachnoid space) in the lumbar region, entry locations may be made in other regions, including the thoracic and cervical regions of the spine. Thus, devices such as catheters, sheaths, and guidewires may pass through any interspace, including the lumbar, cervical and thoracic interspaces. With the needle in place, a guidewire may be introduced into the spinal subarachnoid space through a lumen within the needle. The guidewire may then be directed superiorly and advanced within the spinal subarachnoid space toward the patent's head to a desired location, though in other embodiments the guidewire may be directed inferiorly toward the lower vertebrae. The position of the guidewire within the patient, including within the various regions of the subarachnoid space, may be monitored using any suitable imaging modality, such as magnetic resonance imaging, fluoroscopy, endoscopy, computed tomography, thermal imaging, sonography, X-ray visualization, or any combination of these. Moreover, these imaging modalities can be used throughout a procedure to monitor the positions of other medical devices.

After introducing a guidewire 44 into the subarachnoid space, the operator may dilate the tract created by the guidewire 44 using one or more medical devices suited for that purpose, such as dilators. This may be done after removing the needle. Alternatively, a suitably structured sheath may be introduced over the guidewire for the same dilation purpose and also to facilitate intracranial access with a second device introduced through the passageway of the sheath. If an operator uses a dilator, a medical device such as sheath 24 may be passed over the dilator, and the dilator can then be removed through the passageway of the sheath.

Following sheath placement, techniques applied during other catheter procedures, such as angiography, may be used to navigate the subarachnoid space, including the subarachnoid and intracranial spaces. In this regard, another guidewire may be introduced through the sheath and into the subarachnoid space with a tip that is directed either anteriorly or posteriorly in relation to the spinal cord. A medical device such as a catheter may then be introduced over the guidewire to facilitate intracranial access.

The navigation described above, including one or more of the steps for introducing the various medical devices into the subarachnoid space and advancing those devices within the subarachnoid space and, sometimes, toward the head of the patient, may also be achieved in whole or in part using a robotic device. Furthermore, the representative applications of the present methods discussed below may be carried out in whole or in part using a robotic device. Potential advantages of using a robotic device in this fashion pertain, for example, to navigating through neural tissue. The pial membrane surrounding the brain forms a barrier to penetration, and once the membrane is punctured, there is essentially no resistance to navigation offered by cerebral tissue. Using a robotic device to assist with navigation of the cerebral tissue may be beneficial given the great extent to which the movements of a catheter or guidewire can be controlled using a robotic device and viewed using an imaging modality.

Figure 2A:
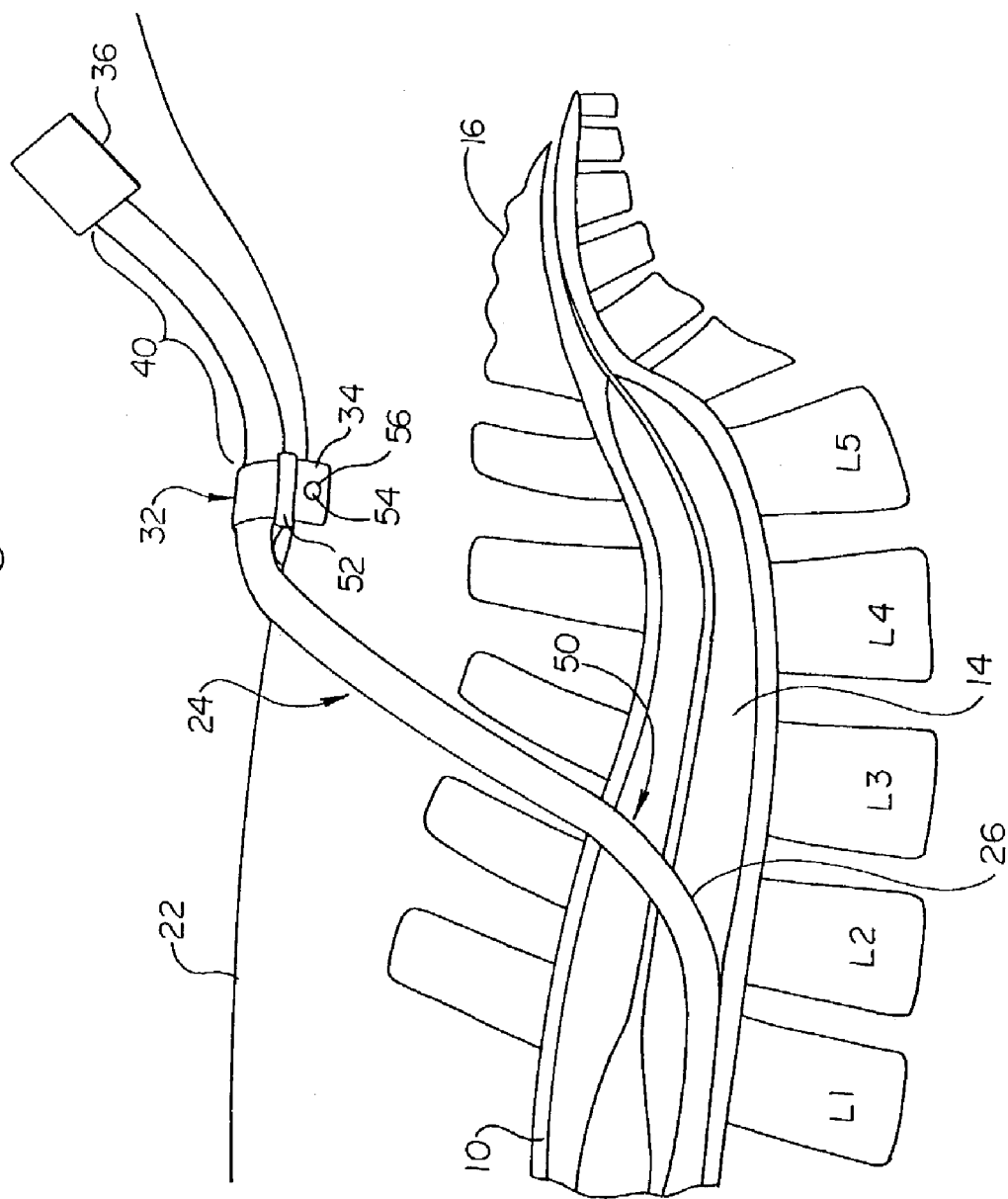
FIGS. 2A and 2B are enlarged views of the lumbar region of the spine shown in FIG. 1, and illustrate a medical device suited for attachment to the skin.

Turning next to FIG. 2A, an enlarged view of a small portion of the central nervous system is illustrated, and example sheath 24 is shown positioned within the subarachnoid space 14. As shown in FIG. 2A, subarachnoid space 14 is the spinal subarachnoid space. The spinal subarachnoid space is located within the bony canal created by the vertebrae. As shown, sheath 24 was percutaneously introduced into the spinal subarachnoid space through dural membrane 10 at entry location 50, and subsequently advanced through the spinal subarachnoid space and toward the head of the patient to facilitate intracranial access by both catheter 24 and guidewire 44. In some embodiments, the sheath 24 is advanced approximately ten centimeters into the subarachnoid space, although greater and lesser distances are used in other embodiments. Skin-attachment apparatus 32, which is coupled to elongated member 26 of sheath 24, is shown as being attached to skin 22 using sutures 54 placed through openings 56 in flexible skin-attachment flap 34. Securing mechanism 52 is shown in FIG. 2A as being used to secure the position of skin-attachment apparatus 32 along elongated member 26. The coupling location of skin-attachment apparatus 32 to elongated member 26 may vary, thereby increasing the versatility of sheath 24 by comparison to sheaths with fixed skin-attachment apparatuses. Furthermore, by spacing apart skin-attachment apparatus 32 from valve apparatus 36, flexible member portion 40 is defined between the two.

Flexible member portion 40 allows the operator to introduce devices through the one or more passageways of sheath 24 at a location that is remote from both the location at which the sheath 24 is attached to the skin 22 and the location at which the sheath 24 enters the skin 22. Some patient motion during the operation can be absorbed by flexible member portion 40. Also, because the length of flexible member portion 40 may be adjusted, the operator can position him or herself remotely from the patient when performing the various steps of the present methods and while permitting the position of various instruments to be monitored via imaging modalities such as magnetic resonance imaging (MRI). Thus, having a suitable length, flexible member portion 40 will allow extension of elongated member 26 from the area of the patient that will be inaccessible during placement of the patient in an MR scanner.

The length of the present flexible member portions, and the distance between one of the present skin-attachment apparatuses and the first end of one of the present elongated members (which distance will differ from the length of the present flexible member portion based on the length of the valve apparatus in question) can be any distance suited to the particular operation. In several embodiments, lengths can range from one up to seventy centimeters, although shorter and longer lengths may be used, too. The related co-pending application Ser. No. 09/905,670 which is incorporated herein by reference, also gives some example lengths. The length of flexible member portion 40 may also be adjusted, for example, to suit the use of sheath 24 with a robotic device. Also included in one embodiment are additional flexible members for attaching to and effectively extending flexible member portion 40, allowing a physician to tailor the particular patient and procedure.

Figure 2B:
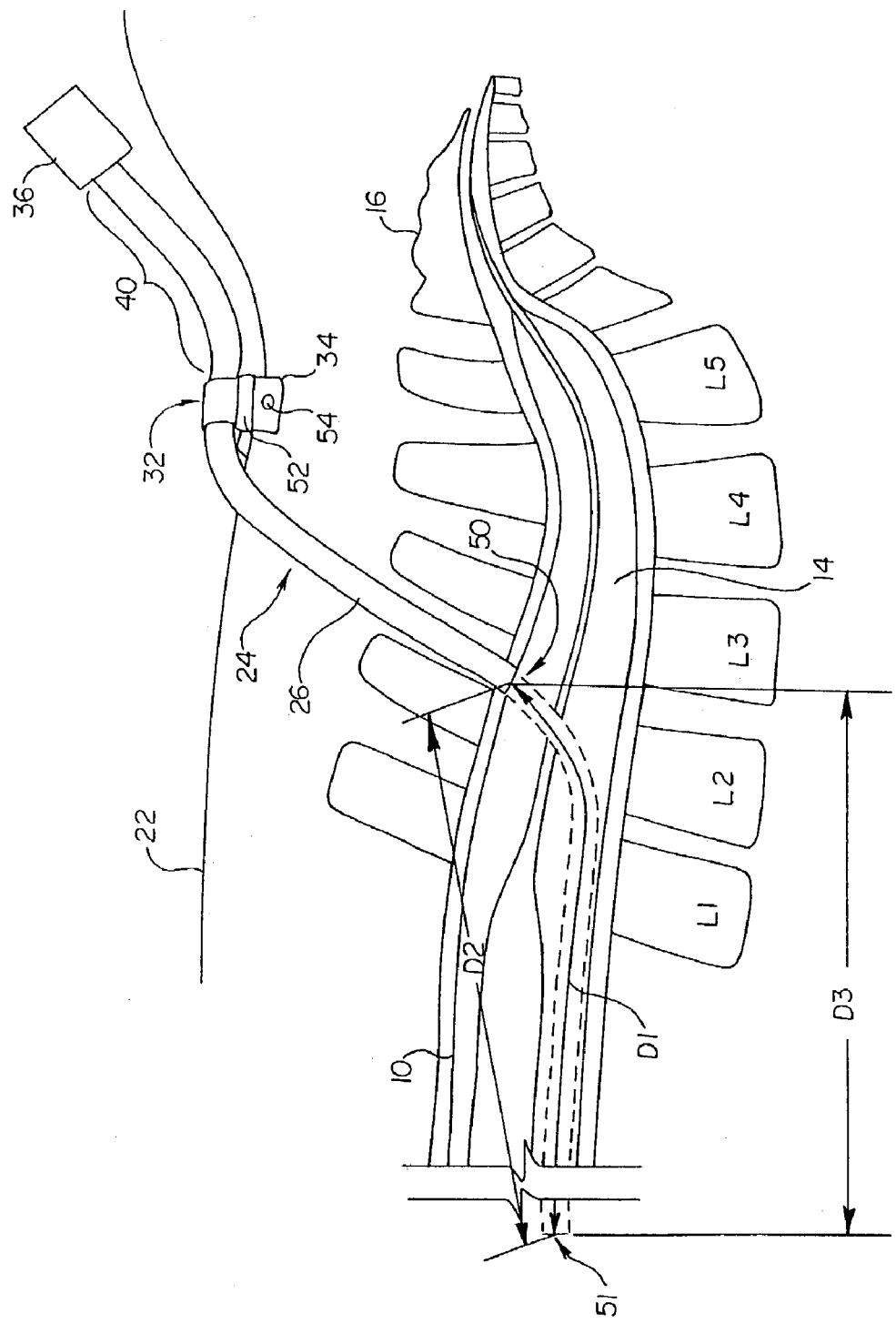

FIG. 2B illustrates sheath 24, which has been percutaneously introduced into subarachnoid space 14 (which, as shown, is the spinal subarachnoid space) at entry location 50. From entry location 50, sheath 24 has been advanced (as shown by the dotted lines) to a second location 51. Devices including catheters and introducer sheaths may be advanced from an entry location by any suitable distance. For some embodiments, a sheath may be advanced more than ten centimeters into the spinal subarachnoid cavity, but other embodiments include advancing by greater or lesser distances. The related copending application Ser. No. 09/905, 670, which is incorporated herein by reference, gives some example distances.

Moving to FIG. 2B, it shows a view similar to that depicted in FIG. 2A. Specifically, FIG. 2B illustrates sheath 24, which has been percutaneously introduced into subarachnoid space 14 at entry location 50. From entry location 50, sheath 24 has been advanced a distance from that entry location to a second location 51. This distance is illustrated in FIG. 2B in terms of D1, which is the distance along the path taken by sheath 24. D1 can be determined by measuring the length of sheath 24 advanced beyond entry location 50. This distance is also illustrated in terms of D2, which is the straight-line distance between entry location 50 and second location 51. This distance is also illustrated as D3, which is the absolute distance toward the head that sheath 24 has been advanced between entry location 50 and second location 51. D3 can be determined by measuring the distance between a plane intersecting entry location 50 and oriented substantially laterally across the longitudinally-oriented patient and a plane intersecting second location 51 and oriented substantially laterally across the longitudinally-oriented patient. Distances D1, D2 and D3 are illustrated in FIG. 2B as examples of the myriad methods one may use to measure distances of penetration or advancement in the present embodiments. For purposes herein, any distance given for advancement or penetration may be measured using, for example, D1, D2 or D3, or any other reasonable measure.

FIG. 3 illustrates a top view of sheath 24. As illustrated in a cut-away section of FIG. 3, elongated member 26 includes a first passageway 58. Valve apparatus 36 is coupled to first end 28 of elongated member 26, and provides a membrane 60 that extends across first passageway 58 in a way that allows other devices to be introduced through passageway 58 while preventing fluid from flowing out of sheath 24 through first end 28. Although membrane 60 is shown as extending across first passageway 58 at a location within first passageway 58, those of skill in the art will understand that membrane 60 could also be positioned outside of first passageway 58 and achieve the same function. For example, although not shown, membrane 60 could be formed as a rubber gasket situated between two elements that screw into each other and vary an opening within membrane 60, thereby providing an adjustable opening valve. Valve apparatus 36 may be coupled to elongated member 26 using, for example, a threaded connection, friction fit, interlocking parts, a clamp, glue, integral formation or other devices or methods of attachment. In addition, valve apparatus 36 may be configured to allow for attachment of flush line 38. This may be accomplished in any fashion, including through the use of a protrusion that is formed as part of valve apparatus 36 and extends away from it (not shown) to which a flush line may be coupled. Valve apparatus 36 may also be configured to allow for fluid communication between flush line 38 and first passageway 58. Alternatively, valve apparatus 36 may also be configured to allow for fluid communication between flush line 38 and a passageway within elongated member 26 other than first passageway 58. Furthermore, valve apparatus 36 may be configured with hub 62 that is configured for attachment to other medical devices such as guidewires, sheaths, catheters, and introducers. The hub 62 may, for example, take the form of a male or female Luer lock piece.

Although only one skin-attachment apparatus 32 is shown for the illustrative embodiment of the present figures, other embodiments may have two or more such apparatuses. Each of these skin-attachment apparatuses may be coupled to elongated member 26. One combination of skin-attachment apparatuses includes permanently attaching one to elongated member 26, and coupling another skin-attachment apparatus in between the permanently-attached skin-attachment apparatus and a valve apparatus coupled to the first end of the elongated member such that the coupling location of the second skin-attachment apparatus is variable. Furthermore, each skin-attachment apparatus may have a flexible skin-attachment flap that is configured for attachment to the skin of a patient. In this regard, while openings 56 are shown in flexible skin-attachment flap 34 for attaching the flexible skin-attachment flap 34 to the skin of a patient, it will be understood that any suitable manner of configuring the flap 34 for attachment to the skin may be used, including the use of a temperature sensitive adhesive, a repositionable adhesive, clips, tape, glue, and the like.

FIGS. 4–9 show different embodiments of skin-attachment apparatus 32. In FIG. 4, skin-attachment apparatus 32, which is configured to be coupled to elongated member 26 at a coupling location and which includes flexible skin-attachment flap 34, is coupled to elongated member 26 such that it is permanently attached to elongated member 26. This may be accomplished by securing flexible skin-attachment flap 34 to elongated member 26 through gluing, integral formation, or the like.

Several additional skin-attachment apparatuses as well as further discussion of examples of introducer sheaths are noted in co-pending application number 10/328,349, filed on Dec. 23, 2002, entitled INTRODUCER SHEATH, which is incorporated herein by reference.

FIG. 5 shows skin-attachment apparatus 32 coupled to elongated member 26 in a way that permits the coupling location of skin-attachment apparatus 32 to elongated member 26 to vary prior to or after attachment of skin-attachment apparatus 32 to a patient's skin. In the illustrative embodiment, skin-attachment apparatus 32 includes flexible skin-attachment flap 34, secondary flap 66, and securing mechanisms 52, which serve to tighten the flaps against elongated member 26 when the mechanisms are engaged. Securing mechanisms may take the form of clips (such as small alligator clips), clamps, flaps that snap together, string, or any other suitable means of temporarily securing flaps 34 and 66 around elongated member 26 in a way that prevents elongated member 26 from moving relative to the flaps until securing mechanisms 52 are disengaged. Padding material, such as a sponge, gelatin-like material, or trapped air may be placed in spaces 68 defined by flaps 66, 34, and elongated member 26, in order to make attachment of skin-attachment apparatus 32 more comfortable to the patient.

Figure 6:
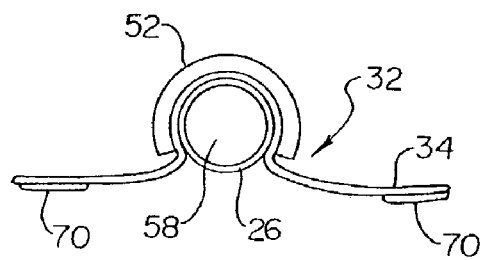
Figure 7:
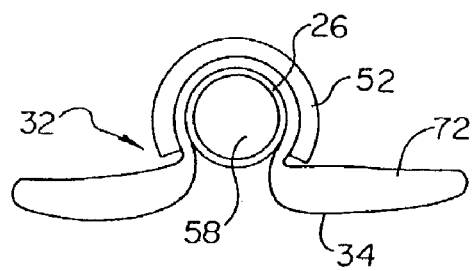
Figure 8:
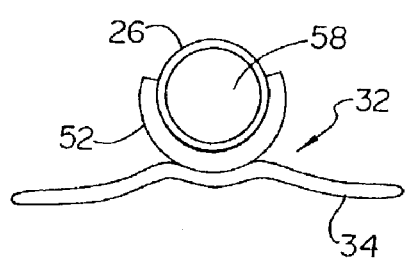

FIGS. 6–8 show skin-attachment apparatuses 32 coupled to elongated member 26 using only one securing mechanism 52. In addition, skin-attachment apparatus 32 in FIG. 6 includes adhesive 70, instead of openings 56 shown in other figures, that is useful in attaching flexible skin-attachment flap 34 to a patient's skin. In FIG. 7, flexible skin-attachment flap 34 contains padding material 72 (as may any of the present flexible skin-attachment flaps), which may increase patient comfort. In both FIGS. 6 and 7, flexible skin-attachment flaps 34 are positioned between elongated member 26 and securing mechanisms 52. In contrast, FIG. 8 shows that securing mechanism 52 may be in direct contact with elongated member 26. In the embodiment shown in FIG. 8, flexible skin-attachment flap 34 may be secured to securing mechanism 52 using any suitable means, including glue, integral formation, and the like. Although not shown in FIGS. 4–9, it should be understood that a flexible skin-attachment flap 34 may be configured in the form of a flap that is folded over elongated member 26 and snapped together, the mating snaps serving as securing mechanism 52.

Figure 9:
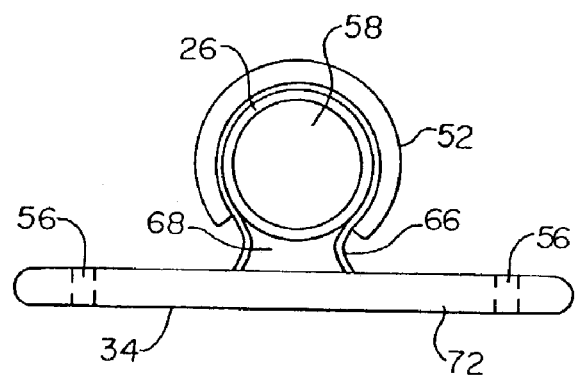

Turning to FIG. 9, the embodiment of skin-attachment apparatus 32 shown includes padding material 72 within flexible skin-attachment flap 34, and may include the same in space 68. Flaps 66 and 34 shown in both FIG. 5 and FIG. 9 may be attached to each other using any suitable method.

Figure 10:
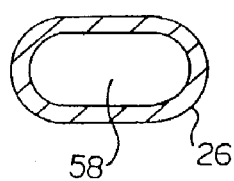
FIG. 10 is a cross-sectional view of an example embodiment of an elongated member of a medical device suited for attachment to the skin, illustrating a non-circular shape.
Figure 11:
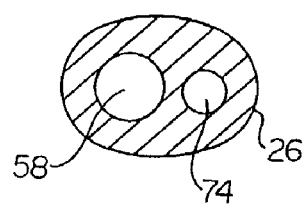
FIG. 11 is a cross-sectional view of an example embodiment of an elongated member of a medical device suited for attachment to the skin, illustrating two lumens.
Figure 12:
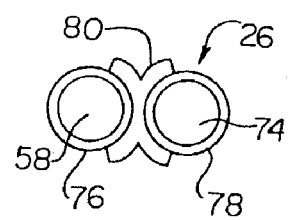
FIG. 12 is an end view showing two sub-elongated members coupled together.

FIGS. 10, 11 and 12 illustrate different embodiments of elongated member 26 of sheath 24. While these figures are described in terms of elongated member 26 and, hence, sheath 24, the embodiments discussed are equally applicable to devices such as catheter 42 depicted in FIG. 1, which may be introduced through the passageways discussed in FIGS. 10–12.

FIG. 10 illustrates a cross section of elongated member 26, revealing that it can have a shape at a given cross section that is non-circular. An elongated member 26 having such a shape along any portion of its length may be well-suited to navigating certain regions within the subarachnoid space that are wider in one dimension than in another, or for navigating through curves or turns, for example. Suitable shapes of cross sections taken at a particular location along an elongated member include oval, and figure-eight shapes, along with other shapes as needed. Furthermore, the present elongated members, and the present sub-elongated members discussed below, may have cross-sectional shapes that vary along the length of the member.

FIG. 11 illustrates another cross section of elongated member 26, revealing that it can have both first passageway 58 and second passageway 74. Elongated member 26 can have additional such passageways consistent with the present methods and apparatuses. Additionally, while the passageways described in this document (including the claims) may extend through openings that coincide with the ends of the particular devices in question (such as sheath 24 and catheter 42 shown in FIG. 1), the openings may in other embodiments be located in positions other than the ends of the present medical devices. Thus, a sheath or a catheter that has one or both ends closed may nevertheless have a passageway therein. Further, though several catheters in the figures having dual passageways are shown in side-by-side configuration, coaxial configurations may also be used, while catheters shown with coaxial configurations may often be replaced equally well with side-by-side configurations.

Turning next to FIG. 12, there is shown elongated member 26 having two sub-elongated members 76 and 78 that are coupled together using coupling device 80, which allows the operator to snap the pieces of tubing together. Other apparatuses for coupling sub-elongated members 76 and 78 may also be used, such as interlocking parts that are integrally formed with the sub-elongated members, interlocking parts that are attached to the sub-elongated members, adhesives that serve to secure the sub-elongated members together but that allow them to be repositioned and re-secured, melting of the sub-elongated members together, glue, and the like. Alternatively, sub-elongated members 76, 78 may be joined, as by bonding during manufacture, such that a cross-sectional configuration of them resembles that shown in FIG. 12, only without a coupling device 80 interposed between sub-elongated members 76 and 78. Sub-elongated member 76 has first passageway 58, and sub-elongated member 78 has second passageway 74. Although many of the illustrative embodiments shown in the figures include round or circular passageways, other shapes including ovals or polygons may be included in other embodiments. Thus, both sub-elongated members 76 and 78 could have cross sections at any location along their length with shapes like the ones depicted in FIG. 10.

Furthermore, as shown in FIG. 13A, sheath 24 can include elongated member 26, which can have first and second sub-elongated members 76, 78 that possess different lengths. As shown, first sub-elongated member 76 has first end 28 and second end 30, and second sub-elongated member 78 has first end 82 and second end 84. FIG. 13A also shows that valve apparatus 36 may be coupled to both sub-elongated members 76, 78, as may be skin-attachment apparatus 32. Furthermore, end 84 is closed, and second sub-elongated member 78 has an opening 86 that together with the opening at first end 82 of second sub-elongated member 78 serves to define second passageway 74.

Figure 13H:
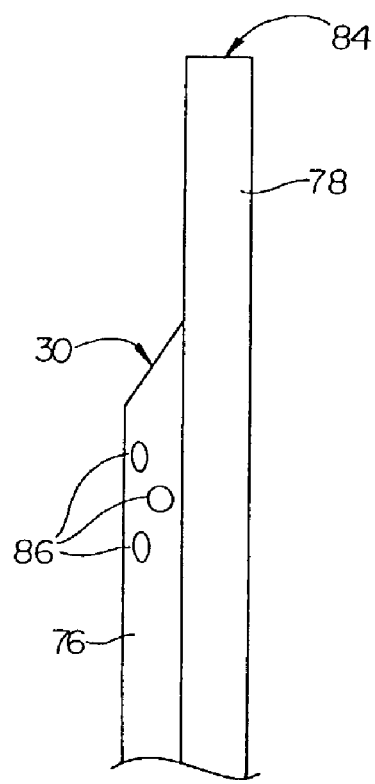

FIG. 13H shows an alternative arrangement for the sub-elongated members 76, 78 of sheath 24 depicted in FIG. 13A. First sub-elongated member 76 has multiple openings 86. First sub-elongated member 76 has a closed second end 30 in FIG. 13H. As explained below, fluid may be introduced through one passageway to a desired location, and withdrawn through another passageway in at least one embodiment. The configuration of sheath 24 illustrated in FIG. 13H may be used during such a procedure, though other sheath configurations could be used, or the sheath could be excluded entirely.

FIGS. 13B–G illustrate several embodiments of the shapes of second ends 30 and 84 of sub-elongated members 76 and 78, respectively. FIG. 13B shows that second end 30 of sub-elongated member 76 may be offset from second end 84 of sub-elongated member 84. FIG. 13B also shows that second end 30 of sub-elongated member 76 may be beveled, or tapered, into sub-elongated member 80, thereby reducing the chance that sheath 24 will "hang-up" on other structures prior to reaching its intended destination. This same benefit may be realized using the configuration of sheath 24 (via sub-elongated members 76 and 78) shown in FIGS. 13C, 13D, and 13G. The configurations illustrated in FIGS. 13E and 13F may be used as the application warrants.

Currently, catheters are available that have compound wall constructions that impart a variable stiffness along the length of the catheter. Catheters are also available with reinforcing material braided into the wall of the catheter to give the catheter greater strength and resistance to kinking. The present devices such as catheter 42 and sheath 24 may have lengths and stiffnesses that vary along those lengths, and they may have walls that include braided materials therein. Also, the present devices such as catheter 42 and sheath 24 may be bendable, and may retain a shape after being bent.

As those of skill in the art will understand, the size of a given passageway of one of the present devices, such as sheath 24 or catheter 42, may be sized appropriately for a given application. Diameters for a passageway within a given device, such as sheath 24, and specifically elongated member 26, and catheter 42, may, for example, range from about 0.01 cm up to about 0.40 centimeters, though larger or smaller diameters are possible for some embodiments. These same dimensions may, for example, serve as the size of either the widest or most narrow dimension of a passageway of one of the present devices, such as sheath 24, elongated member 26, or catheter 42, that has a non-circular shape. The outer diameter of the present devices, such as sheath 24, and specifically elongated member 26, and catheter 42, may vary accordingly, for example up to about 0.50 centimeters, though larger outer diameters could be used as well. These same dimensions may, for example, serve as the size of either the widest or most narrow dimension of the outer surface of one of the present devices, such as sheath 24, and specifically elongated member 26, and catheter 42, that has a non-circular shape. The related co-pending application Ser. No. 09/905,670, which has been incorporated herein by reference, also gives some example inner and outer diameters.

As explained with reference to FIG. 1, for example, the present devices (such as sheath 24 and catheter 42) enter the spinal subarachnoid space after passing through dural membrane 10. In order to close dural membrane 10 after a procedure is complete, the present devices (such as sheath 24, and specifically elongated member 26, and catheter 42) may include a dural closure apparatus. The dural closure apparatus may be coupled to the device in question. The dural closure apparatus may be configured to close the dural membrane as the device is withdrawn from the spinal subarachnoid space. In one embodiment, the dural closure apparatus may be configured to effect closure through movement of a needle, or other suture-delivering apparatus, that is actuated by the operator to cause a suture to be placed through the dura. In another embodiment, the dural closure apparatus may be configured to effect closure through injection of a chemical compound that seals the hole in the dura after the device is withdrawn. One example of a dural closure apparatus that may be modified and coupled to one of the present devices is THE CLOSER (commercially-available from Perclose, Inc., an Abbot Laboratories Company, 400 Saginaw Drive, Redwood City, Calif. 94063).

Figure 19:
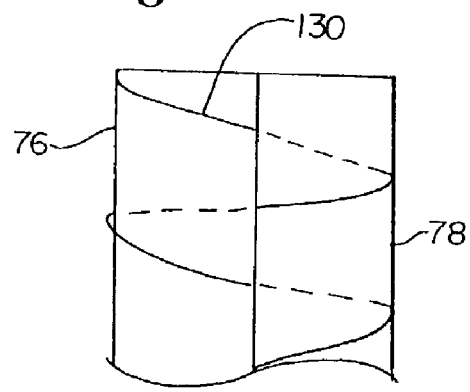
FIG. 19 is a partial side view depicting an embodiment of two sub-elongated members coupled together with a braiding material.
Figure 20:
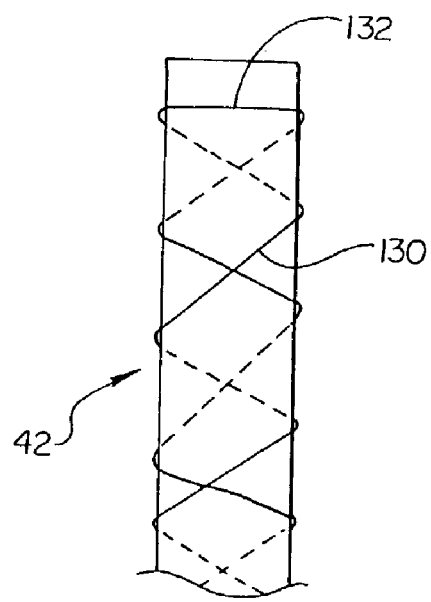
FIG. 20 is a partial side view depicting an embodiment of a catheter wrapped in braiding material.

FIG. 19 illustrates an embodiment of sheath 24 (which, of course, is equally applicable to catheter 42) in which sub-elongated elements 76 and 78 exist, wherein braiding material 130 (which can be a wire) is wrapped around both sub-elongated elements along the length of the sub-elongated elements (the total length not being shown). Such wrapping may appear as a figure eight when viewed from the top. The braiding material may be wrapped as tightly or as loosely as the application warrants, and the tightness of the wrapping may vary along the length of sheath 24, thereby imparting the sheath with a variable stiffness and flexibility. The same type of wrapping may be applied to a catheter having only one passageway, as illustrated in FIG. 20. There, the wrapping may be achieved using a single wire that is placed in contact with the wall of catheter 42 at roughly the mid-point 132. Then, the two halves of braiding material 130 may be crisscrossed to achieve the desired braiding, varying the tightness of the wrapping as desired to affect the stiffness of catheter 42. Alternatively, one end of braiding material may be placed in contact with catheter 42 near the end shown in FIG. 20, and the braiding may be achieved by winding the free end of the braiding material once around the catheter, then back up so as to cross the already-formed loop, then back down slightly further, and back up in the same fashion, repeating the process to achieve the desired braiding. Again, the tightness of the wrapping (which may be thought of as the closeness of the braiding material segments to each other) may be varied to vary the stiffness of the catheter. The braiding, as is known in the catheter arts, may include a multitude of variations and can be embedded into a catheter material making up the outer elongate member of a catheter by various techniques. It may also be contained within an outer elongate member.

The braiding pattern or material used may affect the MR-visibility of the resulting catheter or sheath. The sub-arachnoid space is filled with CSF that is relatively static and is of very high signal intensity on T2-weighted images. While a material that presents a signal void on MR could not be seen on either T1- or T2-weighted fluoroscopy in the vascular space (flowing blood has a signal void in either of these settings), a material that has a signal void is very conspicuous on T2-weighted imaging in the subarachnoid space. Platinum is a metal that is appropriate for enhancing the MR-visibility of the present devices. Additionally, other metals having low signal intensity may be appropriate. For example, non-ferromagnetic stainless steels, nitinol, stainless steel or kevlar, among other materials, may be used for the braiding material 130.

Medical devices including but not limited to the catheters and sheaths discussed herein that have two or more passageways may enable the use of an endoscope in one passageway to observe, for example, a manipulation conducted using a device introduced through the other passageway, or even the position of the other sub-elongated member that has the other passageway. Medical devices that have two or more passageways may also permit a fluid to be introduced in one passageway and withdrawn via the other passageway. Medical devices that have two or more passageways may allow the introduction of a guidewire in one passageway and another, therapeutic device in the other passageway. Interaction between functions conducted via each passageway may be achieved such that the functions work together, or complement each other, to achieve a therapeutic goal.

Furthermore, medical devices such as sheaths and catheters that have the configurations discussed in FIGS. 11 and 12 (i.e., that have two or more passageways) have vascular applications, too. For example, there are currently instances in aneurysm treatment in which one catheter is introduced via one femoral artery for placement within an aneurysm and another catheter is introduced via the other femoral artery for introduction of a balloon across an aneurysm neck. Using a device other than a balloon to assist the aneurysm coiling, an apparatus may be introduced via one passageway of a medical device such as a sheath or catheter that has one of the configurations discussed in FIGS. 11 and 12 (i.e., that has two or more passageways) to improve an aneurysm neck while a coil is introduced via the other passageway, thus achieving via a single femoral artery access that currently requires bilateral access. Furthermore, this aneurysm embolization may be achieved using a sheath or catheter that includes 2 sub-elongated members whose distal portions are spaced apart from each other, as in a "Y" shape.

Figure 18:
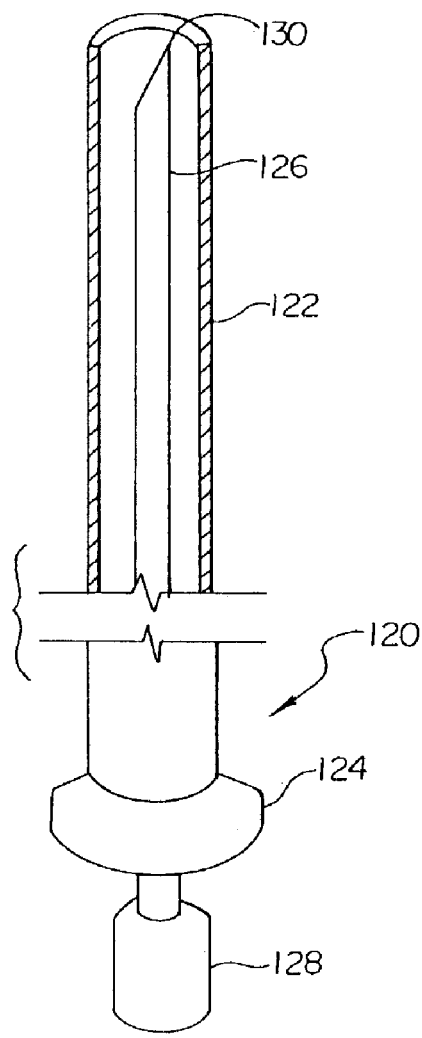
FIG. 18 depicts an example embodiment of a penetration apparatus.

FIG. 18 illustrates a penetration apparatus 120 that may be useful in penetrating various membranes that may be encountered using the present methods. Penetration apparatus 120 includes outer sleeve element 122, outer sleeve element hub 124 coupled to outer sleeve element 122, inner puncture element 126, and inner puncture element hub 128 coupled to inner puncture element 126. Outer sleeve element hub 124 may be configured to be slidably coupled to inner puncture element 126 (such that outer sleeve element 122 may slide along, and then be locked against, inner puncture element 126), and inner puncture element hub 128 may be configured to be slidably coupled to another device introduced through the passageway (not shown) of inner puncture element 126. Inner puncture element may be provided with a passageway sized to slidably receive at least a guidewire. Alternatively, the inner puncture element may be a coaxial element such that the outer or inner component acts as a guidewire in addition to a puncture element or component.

One membrane that may be punctured by operating penetration apparatus 120 is the pia mater, which is a membrane surrounding the brain that is fragile in some locations and tough in others. Distal tip 130 of inner puncture element may be configured to be sharp enough to penetrate the pia mater at any location therealong without exerting a degree of force or manipulation that results in damaging brain tissue. In operation, a device (such as sheath 24 or catheter 42) including a first passageway may be percutaneously introduced into the spinal subarachnoid space at an entry location and advanced within the subarachnoid space; then penetration apparatus 120 may be advanced through the first passageway of the device, and a membrane, such as the pia mater, may be punctured using penetration apparatus 120. Penetration apparatus 120 may be advanced along a guidewire, or it may simply be advanced through the first passageway, to the edge of the membrane; inner puncture element 126 may be further advanced until it punctures the membrane; inner puncture element may then be refracted into outer sleeve element 122 and penetration apparatus 120 advanced through the plane of the punctured membrane, or outer sleeve element 122 may be advanced over inner puncture element 126 through the plane of the punctured membrane. Outer sleeve element 122 may then act as a guidewire for a device such as catheter 42 as the same advances into the brain substance. The preceding steps may be further facilitated by the use of anchoring devices or a guide catheter such as those illustrated by copending patent application Ser. No. 10/328,373 filed on Dec. 23, 2002, entitled GUIDE CATHETER FOR INTRODUCTION TO THE SUBARACHNOID SPACE, which is incorporated herein by reference.

The material that may be used for the inner and outer elements of penetration apparatus 120 may, for example, be metallic or polymeric, such as plastic. Suitable materials for both outer sleeve element 122 and inner puncture element 126 include nitinol, stainless steel, and gold. A platinum plating, for example, may be included to enhance radiographic visibility. If an imaging modality such as MRI or radiographic visualization (e.g., fluoroscopy), the imaging modality used may impact the materials used in the construction of the elements of penetration apparatus 120, for example, in an MRI apparatus it may be desirable to use a non-magnetically reactive material in construction of these several elements.

Another embodiment of penetration apparatus 120 that is not shown in FIG. 18 differs from the embodiment shown in FIG. 18 in the manner in which the inner and outer elements 126 and 122 are interrelated. In this additional embodiment, inner puncture element 126 may be coupled to outer sleeve element 122 with a mechanism that allows inner puncture element to be "fired," or advanced rapidly, a few millimeters to achieve rapid penetration. In yet another embodiment of penetration apparatus 120 not shown in FIG. 18, inner puncture element 126 is coupled to outer sleeve element 122 using threads to allow for finely-controlled advancement of inner puncture element 126. These embodiments for penetration apparatus 120 are included herein for illustrative purposes; other structures may be used and still be within the spirit.

At least some embodiments of the present methods will offer many advantages over conventional methods of surgically accessing the intracranial and spinal subarachnoid space, which have historically included a skin incision, dissection to either the cranium or spinal bony covering, removal of some bone, and dissection through the meninges to gain access to the neurological structures. For example, some embodiments of the present methods do not require a craniotomy and a brain retraction, which are typical for conventional approaches to brain surgery. Further, at least some embodiments will also enable operators to surgically approach the brain from a remote location, such as from a lumbar puncture, for instance, and make it possible to perform such surgery in an MR scanner without interference from magnets in the surgical field. Physicians may also access areas of the brain that are difficult to reach from a craniotomy approach and some embodiments may enable some procedures (for example, subarachnoid space lavage, etc.) not easily performed via craniotomy.

The following examples of representative applications may be performed using a variety of devices, some illustrative examples of which have been discussed above. Additional devices and methods adapted for particular applications are further explained below. Depending on the application, the devices used may be treated so as to maximize their visibility via a given imaging modality, such as MRI or radiography (e.g., fluoroscopy).

Furthermore, it will be understood that for a given application, it may be feasible to introduce one device into the subarachnoid space at one entry location, and later, or simultaneously, introduce another device into the subarachnoid space at a different entry location, thereafter using the devices together to achieve a therapeutic result. For example, in altering the temperature of at least some brain tissue, discussed below in greater detail, it may be possible to introduce a fluid through the passageway of one device introduced into the subarachnoid space (such as the spinal subarachnoid space) at one entry location, and withdrawing fluid through the passageway of another device introduced into the subarachnoid space (such as the spinal subarachnoid space) at another entry location. As another example, in flushing CSF as described below, it may be beneficial to use two passageways of a sheath or catheter having multiple passageways to deliver fluid to a target area. Further, this may be achieved using a sheath or catheter that includes 2 sub-elongated members whose distal portions are spaced apart from each other, as in a "Y" shape. Fluid may be withdrawn through the passageway of a device introduced at a different entry location, or fluid may be withdrawn through a third passageway within the sole sheath or catheter.

Flushing of CSF to Alleviate Vasospasm

A major complication of subarachnoid hemorrhage is vasospasm, which is related to the presence of blood in the subarachnoid space surrounding cerebral blood vessels. One treatment that is used to help alleviate vasospasm entails the lavage of the CSF within the subarachnoid space with both saline and hemolytic agents to remove the blood, accessing the CSF, for example, by removing bone from the skull to create an entry location. Using the present methods, it may be feasible from a percutaneous spinal approach to catheterize the subarachnoid or intracranial space in the region of a hemorrhage or clot and perform lavage from that approach without craniotomy. For example, after introducing a device, for example, sheath 24 or catheter 42 discussed in relation to FIG. 1, into the spinal subarachnoid space at an entry location and advancing that device within the spinal subarachnoid space a distance from the entry location, saline and/or material having hemolytic agents may be transferred through a passageway of the device toward the region of the hemorrhage or clot in order to flush the relevant CSF.

Modifying the Temperature of at Least Some Tissue

One example of modifying the temperature of at least some tissue, for example tissue in the brain or spinal column, is inducing hypothermia in at least some such tissue. The potential beneficial effects of hypothermia in protection against injury are well known, both in the public domain and in the medical literature. The most commonly encountered instance in the uncontrolled environment is probably in near drowning. In these situations, survival is enhanced in cold water because the metabolism is slowed and hypoxia is better tolerated. In neurosurgical practice, hypothermia is used therapeutically to prolong cerebral vascular occlusion times that can be tolerated during aneurysm surgery. However, most traditional neurosurgical techniques are unable to create isolated cerebral hypothermia. Thus, whole-body hypothermia is used, often in association with circulatory arrest, with many attendant risks.

Some examples of the present methods can be used to modify the temperature of at least some tissue. Such a modification may be achieved by flushing selected tissue with a fluid that may be temperature-controlled, such as saline or the subject's own CSF, which may be drained from a different location. The fluid may be introduced through a device introduced into the spinal subarachnoid space. For example, after introducing a device having at least one lumen, such as a catheter or sheath into the spinal subarachnoid space and advancing that device within the spinal subarachnoid space a distance from the entry location, the temperature of at least some brain tissue may be modified by introducing a temperature-controlled fluid through the lumen.

In one example embodiment for cooling selected tissue, the device introduced may include a catheter having two lumens. One example of such a catheter is shown in FIG. 21A. The illustrative infusion catheter 200 includes a first lumen 202 and a second lumen 206. The first lumen 202 ends at a first port 204 near the distal tip 201 of the catheter 200, while the second lumen 206 ends at a second port 208 at a more proximal position in relation to the distal tip 201 of the catheter. In operation, CSF from the patient undergoing treatment is drained through the second lumen 206, while a cooling fluid is introduced through the first lumen 202.

The cooling fluid may be the patient's own CSF, as is shown in FIG. 21A. CSF is drained from within the patient's subarachnoid or intracranial space via the second lumen 206, and the second lumen 206 feeds the CSF into a pump 210 which in turn feeds a heat exchanger 212. The heat exchanger 212 cools the CSF down to a desired temperature. In some embodiments the infused fluid temperature may be anywhere down to about thirty-two degrees Fahrenheit. For other embodiments not necessarily aimed at inducing cooling, the CSF may also be warmed up to a temperature up to about one hundred and thirty degrees Fahrenheit; the induced heat may, for example, accelerate cellular metabolism in, prompt cellular growth near, or induce increased blood flow to desired areas. CSF then leaves the heat exchanger 212 and enters the first lumen 202, through which it is reintroduced to a different area of the patient's subarachnoid or intracranial space via the second port 204 at the distal end 201 of the catheter 200.

The heat exchanger 212 can include any structure or device that is adapted to provide the desired temperature to the CSF. Some examples of heat exchange structures include coils, tube-in-tube, radiator styles, and other such heat exchange devices. Likewise, the pump 210 can include any pump or like device that is adapted to provide the desired flow of CSF. Some examples of pump structures include mechanically, magnetically or electrically powered impellers, diaphragms, bulbs, and the like. In some embodiments, an infusion apparatus or other apparatus for use, for example, in exchanging CSF or causing a temperature change in at least some CSF may be introduced using a guide catheter adapted for such use, for example, a guide catheter as noted in co-pending application Ser. No. 10/328, 373 filed on Dec. 23, 2002 entitled GUIDE CATHETER FOR INTRODUCTION TO THE SUBARACHNOID SPACE AND METHODS OF USE THEREOF, which is incorporated herein by reference.

In additional embodiments, a filter element may be included for filtering the CSF of undesired substances, for example, blood leaking from an injured blood vessel. For example, such a device could be used in flushing of CSF to alleviate vasospasm as discussed above. In other embodiments, a drug, antibiotic or radiopaque substance, for example, may be mixed with the re-introduced CSF and thereby infused into the subarachnoid space. In other embodiments, the patient's CSF may be drained and replaced by another fluid. The fluid replacing the CSF can be chosen from a variety of biocompatible fluids. For example, saline may be introduced. Again, drugs, antibiotics or radiopaque materials may be included as well.

During operation, the infused fluid may cause damage to adjacent tissue if the pressure of the fluid when leaving the catheter 200 is not controlled. One method/device for controlling exit pressure of the fluid is also shown in FIGS. 21A–C. FIG. 21B illustrates a cross sectional view of catheter 200 at a section proximal of the second port 208. The first lumen 202 may occupy a lesser area of the cross section in this region than the second lumen 206, although the exact ratios may vary in other embodiments. Distal the second port 208, at location 220, the cross sectional disposition of the catheter 200 changes to resemble that shown in FIG. 21C. Notably, now the first lumen 202 occupies most of the available space. Because the cross sectional area of the lumen 202 through which fluid is flowing has increased substantially, the pressure within the lumen is reduced, and the likelihood of fluid exiting the catheter 200 at first port 202 causing damage to adjacent tissue is reduced. Other apparatuses and methods for reducing tissue damage caused by pressure jets of exiting fluid include the addition of throttling members to perforations or ports of fluid infusion catheters, use of varying sized perforations, and other structures or designs for so doing, including, for example, variation of the material chosen for constructing the fluid infusion catheter or addition of coatings such as a hydrophilic coating to an area near the exit port.

FIGS. 21D–E illustrate another example embodiment of the present invention, this embodiment comprising a closed system. The illustrative cooling catheter 220 includes a first lumen 222 and a second lumen 224. A pump 230 is also shown, again feeding into a heat exchanger 232. As shown by the arrows, fluid flows from the proximal end where pump 230 and heat exchanger 232 are toward the distal end 234. Distal end 234 includes a heat exchanging element 236. The heat exchanging element 236 may be characterized, as shown, by an irregular shape providing increased surface area. Heat exchanging element 236 may also be of a different or thinner material than the rest of the illustrative cooling catheter 220, for example, to provide for improved thermal conductivity. The illustrative embodiment of FIG. 21D includes the heat exchanging element 236 as purely illustrative, and the heat exchanging element may take on a variety of shapes or designs, some of which are further illustrated, for example, in FIGS. 23–29.

In some embodiments, heat exchanging element 236 may have a rigid shape, while in other embodiments the heat exchanging element may be a flexible membrane, an inflatable member, or a collapsible unit. For example, in some embodiments the heat exchanging element 236 may be a collapsible member that, once disposed at a desired location, may be expanded to increase the surface area of the heat exchanging element. Also as shown, the distal end of first lumen 222 may end in a membrane 238 that could control fluid flow, for example, if membrane 238 were a unidirectional flow element that prevented back flow of fluid through first lumen 222. Membrane 238 may also serve to diffuse fluid flow, directing the fluid flowing from lumen 222 into heat exchanging element 236 towards a desired portion or area of the heat exchanging element 236.

FIG. 21E shows that the lumen cross sectional areas for the first lumen 222 and second lumen 224 may be different in at least one illustrative embodiment. In other embodiments, the relative lumen sizes may vary widely, as may the lumen shapes, which need not be of a circular cross section. For example, angular, oval and other shapes may be used for cross sections of the first lumen 222 or second lumen 224, and these shapes may vary along the length of the illustrative cooling catheter 220.

Figures 22A, 22B, 22C:
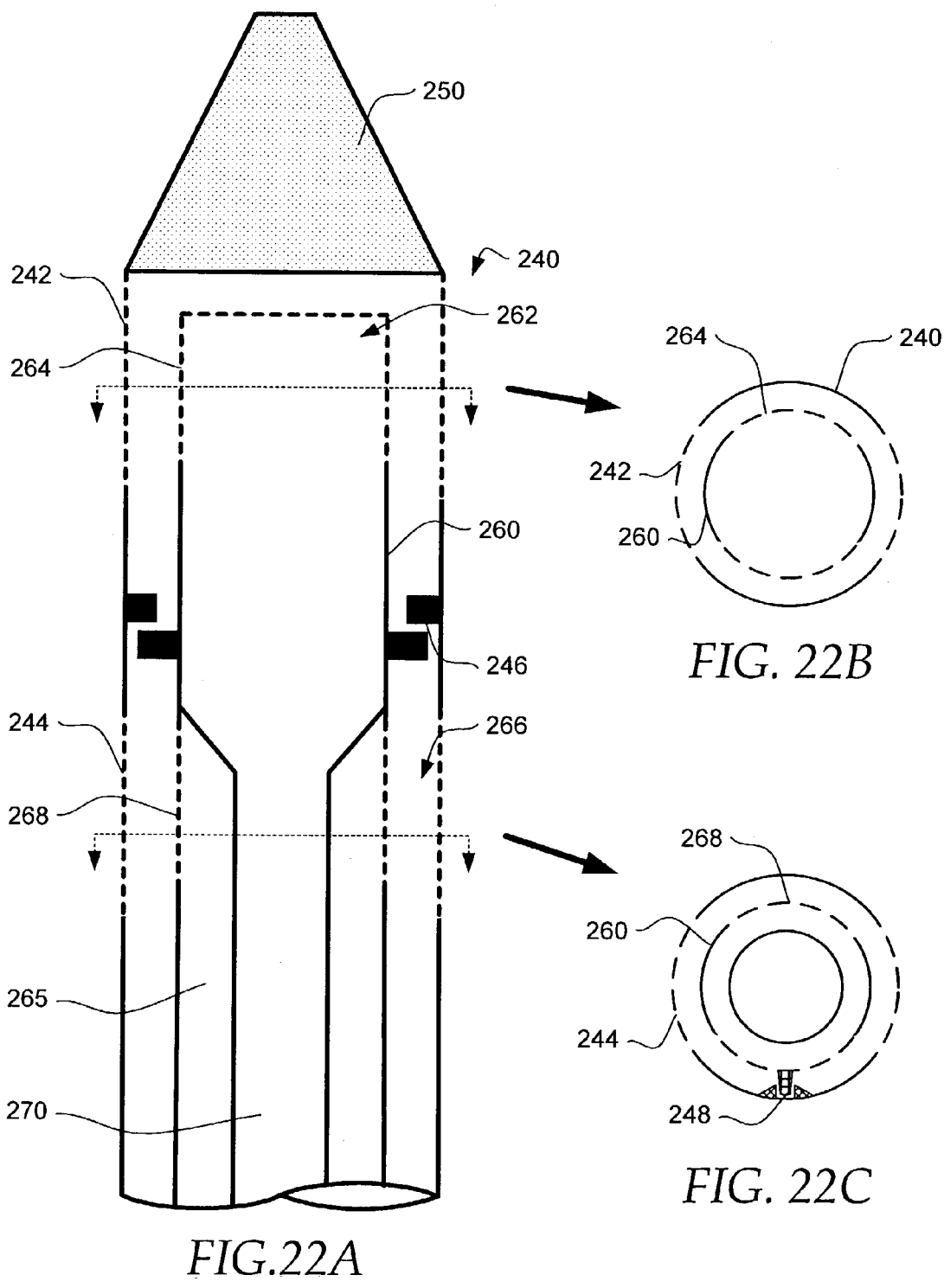
FIG. 22A is a partial side view of an illustrative embodiment of a fluid exchange catheter including a diffusing catheter.
FIGS. 22B and 22C are cross sectional views of portions of the catheters of FIG. 22A.

FIGS. 22A–C illustrate another example embodiment of a catheter adapted for infusion or lavage usage, or the like. In the illustrative embodiment, a diffusing catheter 240 is introduced first, and a dual lumen catheter 260 having two lumens 265, 270 is introduced second. The diffusing catheter 240 is introduced to shield the surrounding tissue from pressure jets produced by fluid flowing out of and into the dual lumen catheter 260. The diffusing catheter 240 includes perforations 242, 244 for allowing the fluid leaving the dual lumen catheter 260 to escape across a broader area, thus reducing the jet-flow induced irritation of local tissue. The diffusing catheter 240 may include stops 246 for sealing off the area of induced cooling near the distal end 250 from other portions of the diffusing catheter 240. The stops 246 may also include a lock (not shown) for locking the dual lumen catheter 260 into place once it is introduced inside the diffusing catheter 240.

In another embodiment further illustrated in FIGS. 22A–C, diffusing catheter 240 and dual lumen catheter 260 include fitting members 248 (shown in FIG. 22C) to cause a specific axial orientation of the dual lumen catheter 260 with respect to the diffusing catheter 240. One motive behind assuring specific axial orientation is to reduce fluid jet flow pressures caused as fluid enters or exits the dual lumen catheter 260. One set of perforations 242 of the diffuser catheter 240 longitudinally corresponds to a first port 262, including perforations 264, of the dual lumen catheter 260. The desired axial alignment, shown in FIG. 22B, causes one set of perforations 242 of the diffuser catheter 240 to be misaligned with respect to the perforations 264 at the first port 262 of the dual lumen catheter 260. Likewise, as shown in FIG. 22C, the desired axial alignment causes the other set of perforations 244 of the diffusing catheter 240 to be misaligned with respect to perforations 268 at the second port 266 of the dual lumen catheter 260. In this manner, fluid leaving the dual lumen catheter 260 does not have a straight-line path to surrounding tissue. Note that the diffusing catheter 240, while shown in this embodiment, is not required in all embodiments.

A feature which is also illustrated in FIG. 22A is the varying cross sectional area of the first lumen 270 of dual lumen catheter 260, which in particular occurs distal the end of the second lumen 265. As illustrated in FIGS. 21A and 22A, the dual lumen catheters described herein may be side-by-side catheters or coaxial catheters, whichever is desired. An additional feature that may be included in many of the catheters shown herein is the inclusion of a flexible distal tip 250, which may include a tapered section, as shown in FIG. 22A. A flexible distal tip 250 may be used, for example, to reduce any irritation caused by navigation of a catheter through the soft tissues, membranes, and fluid filled areas of the subarachnoid and intracranial spaces. Though not specifically shown in all figures, many of the catheters described herein may be introduced after a guidewire has been advanced to a desired area. Such catheters may be introduced over-the-wire, in a monorail configuration, or by other guidewire introduction methods widely known in the vascular catheterization arts, including, for example, so-called rapid exchange configurations also known with respect to biliary catheters.

For the above noted methods and devices, two catheters of different (or even the same) lengths could be used in place of the dual lumen catheter. One advantage of such a system is that the two catheters could be more cheaply made, for example. A second advantage is that one of the catheters could be replaced during an operation to change the position of one or both catheter ports, allowing different areas of the subarachnoid or intracranial spaces to be drained or to receive infused fluid at different times of a single procedure. One advantage of such changes would be to reduce irritation at a single location by only pumping fluid at that location for a shorter period of time, or to allow a different location to be infused with fluid as needed during an operation without losing the location of fluid drainage.

A pumping apparatus may be utilized in the process of modifying the temperature of at least some tissue to assist in maintaining pressures and temperatures within the subarachnoid space. This pumping apparatus may be coupled to the device through which the fluid is introduced. For at least one embodiment, the pumping apparatus may include two independently-controlled, calibrated pumps that may be coupled to a hub adapter coupled to, for example, the device through which the fluid is introduced. To control the intracranial fluid volume, the volume of fluid pumped into the subarachnoid space may be matched by an equal volume that is withdrawn from the subarachnoid space. This pumping apparatus may be configured to achieve this balance with flow monitors and flow controls, even in circumstances in which the outflow may be achieved without introducing negative pressure at the outflow site. Further, in this regard, this pumping apparatus may be configured to operate with pressure monitors and pressure controls that enable both the measurement of intracranial pressures and the manipulation of the same. In addition, this pumping apparatus may be configured to operate with temperature monitors and temperature controls that enable both the measurement of intracranial temperatures and the manipulation of the same. In this regard, the pumping apparatus may be configured to operate with temperature monitors and temperature controls that enable both the measurement of infused fluid temperatures and the manipulation of the same.

Flow rates as low as a fraction of a cubic centimeter per second or as high as multiple cubic centimeters per second may be achieved with this pumping apparatus, though pressures exceeding two hundred millimeters mercury are considered unlikely since this would exceed intracranial pressures likely to be compatible with life. Infused liquid temperatures varying between thirty-two and one-hundred and thirty degrees Fahrenheit may be achieved using this pumping apparatus, for example. In another illustrative embodiment, the infused liquid temperatures may exceed this range, but may fail to cause damage because of heat exchange occurring with tissue (when internal to the subject) and air (when external to the subject) and the infusing catheter. While it is contemplated that the internally caused temperature change to tissue may in some instances be limited by tissue-damage tolerances, it may also be noted that, in other embodiments, the infusion of a very hot or very cold fluid, or heat exchange with a very hot or very cold element may be used to ablate or cauterize a desired tissue area or volume, with such procedures using temperatures that may vary even more widely.

Some examples of internally disposed fluid displacement apparatuses and/or heat exchangers are illustrated in FIGS. 23–27. These illustrative examples are included merely to display certain features, and should not be construed to limit the invention to their structures. Variously illustrated are methods for using a heat exchanging fluid to cause heat exchange without removing CSF from the subarachnoid and cranial spaces, methods for introducing a collapsible fluid displacement apparatus, and devices that integrate both a heat exchanger and a fluid displacement apparatus into one structure. In at least some embodiments, where an insertable heat exchange element is used, it can be desirable to create movement or displacement of the CSF about the inserted heat exchange element to enhance heat transfer. One additional aspect of several embodiments not shown in several figures is the possible inclusion of small sensors for sensing local temperature and pressure, both of which are factors that may be important to monitor in some applications of these pumping and infusing apparatuses. The inclusion of temperature or pressure sensors is not necessary to the practice, but can be useful in some applications.

Figure 23A:
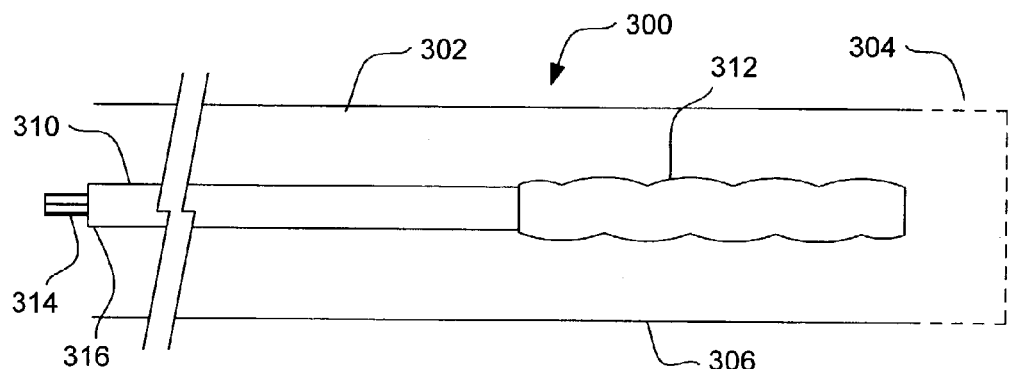
FIGS. 23A–C are partial side views of an example embodiment of a catheter including an expandable member in different states of expansion.
Figure 23B:
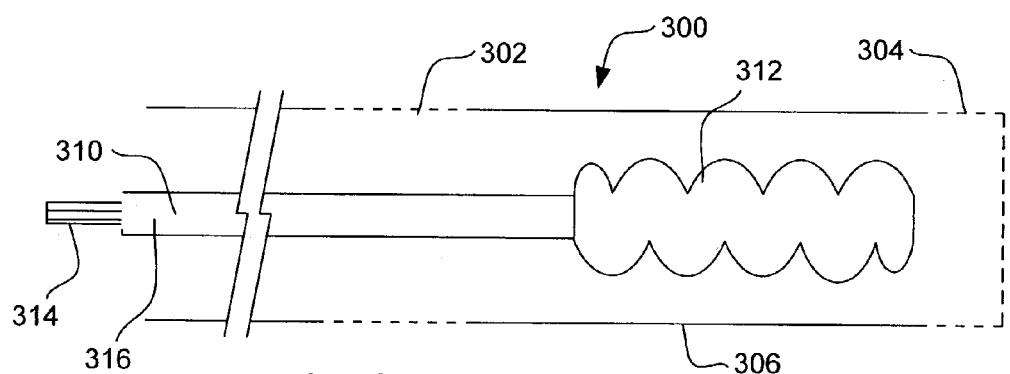
Figure 23C:
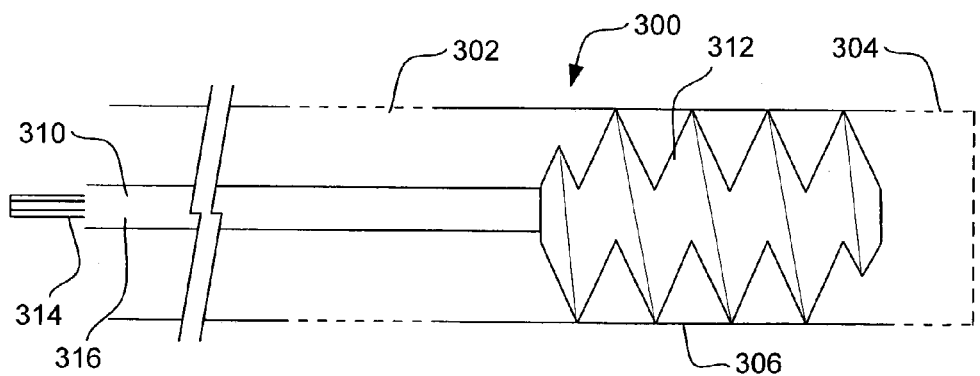

FIGS. 23A–C show a collapsible fluid displacement and heat exchange apparatus and illustrate a method of its use. Outer catheter 300 is shown including first port 302 and a second port 304, the second port 304 coinciding with the distal end of the outer catheter 300. In other embodiments, the outer catheter 300 may include a distal tip (not shown) extending beyond second port 304. Inserted inside outer catheter 300 is an inner catheter 310 including an inflatable member 312 in fluid communication with a lumen 316 and mechanically connected to a wire 314. As shown, the inner catheter 310 is disposed so that the inflatable member 312 is located along an intermediate section 306 of the outer catheter 300 that is between the two ports 302, 304.

In FIG. 23A, the inflatable member 312 is deflated, and both outer catheter 300 and inner catheter 310 can be supposed to be disposed inside the subarachnoid or intracranial spaces of a subject. As shown, in FIG. 23B, the inflatable member 312 is partially inflated. The inflation may be performed by infusing an inflation fluid through the lumen 316 into the inflatable member 312. The inflation fluid may be infused at a temperature that is different from the temperatures of the surrounding tissue, for example, it may be at a cold temperature to impart localized cooling of the CSF and tissue, or it may be at an elevated temperature to impart localized warming. The inflatable member 312 may be constructed of a material suitable for performing heat exchanging functions, and may be chosen to match particular needs of a given patient, or may be chosen depending upon the desired temperature change that is to be effected. The inflation fluid may be any suitable fluid, for example, inflation fluids used typically in vascular inflation balloon procedures. The inflation fluid may also be a saline mix or CSF to enable the inflation fluid to be easily accepted by local tissue if it escapes due to inflatable member 312 or lumen 316 defect or failure. In operation, the inflatable member 312 may be periodically inflated and deflated to infuse fresh cooling or heating fluid inside the inflatable member 312. A temperature sensor (not shown) may be disposed to monitor the temperature inside inflatable member 312 and determine when fresh cooling or heating fluid is needed.

Upon fuller inflation, as shown in FIG. 23C, the outer portions of the inflatable member 312 are adjacent to or in slidable contact with the inner wall of catheter 300 at intermediate section 306, and inflatable member 312 takes the form of an Archimedean screw. While contact is not necessary to attain a fluid displacement function, slidable contact or engagement with the intermediate section 306 may improve displacement efficiency. The illustrative embodiment shows at least two methods for displacing fluid with the inflatable member 312. In one method, the inflatable member 312 is inflated, pushing fluid towards the second port 304 from the first port 302. In another method, rotating the wire 314 causes rotation of the inflatable member 312, which in turn displaces fluid from the first port 302 toward the second port 304. As the fluid passes over the inflatable member 312, heat exchange performance is enhanced by the long contact from proximal to distal end of the inflatable member 312.

When fully inflated, the inflatable member 312 may have a length of in the range of about ten to fifty millimeters, while larger or shorter lengths may be used. The diameter of the inflatable member 312, when inflated as shown in FIG. 23C may be in the range of about one to three millimeters, although in the embodiment as shown the limit of the balloon diameter may include the inner diameter of intermediate section 306. In one embodiment, the inflatable member, when fully inflated, has a length in the range of twenty to twenty five millimeters and a diameter in the range of one and a half to two millimeters. The material of which intermediate section 306 is made may include elastic properties for allowing the inflatable member 312 to expand to a greater diameter than the overall catheter would ordinarily have.

While the illustrative embodiment of FIGS. 23A–C shows an inflatable member 312 inflated by passage of fluid through a single lumen 316, other designs may also be used. For example, a multi-lumen inflation scheme may be used where one lumen provides for inflow of fluid while a second lumen allows for outflow of fluid, for example, as described below with reference to FIG. 26. Such embodiments may provide for better heat exchange, for example, by enabling continual or complete inflation fluid replacement or flushing. For example, where a single lumen is used to inflate and deflate an inflatable member, it may be difficult to extract all of the inflation fluid from both the inflatable member and the single lumen, so that when inflation begins again, the inflatable member may receive some amount of untreated fluid that remained within the lumen or inflatable member; such re-use without extraction of the fluid may impede heat transfer.

Figure 24:
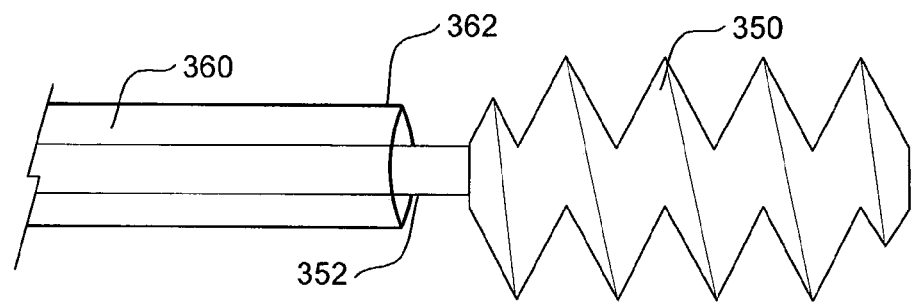
FIG. 24 is a partial side view of an example embodiment of a catheter including an expandable member disposed past the distal tip.
Figure 26:
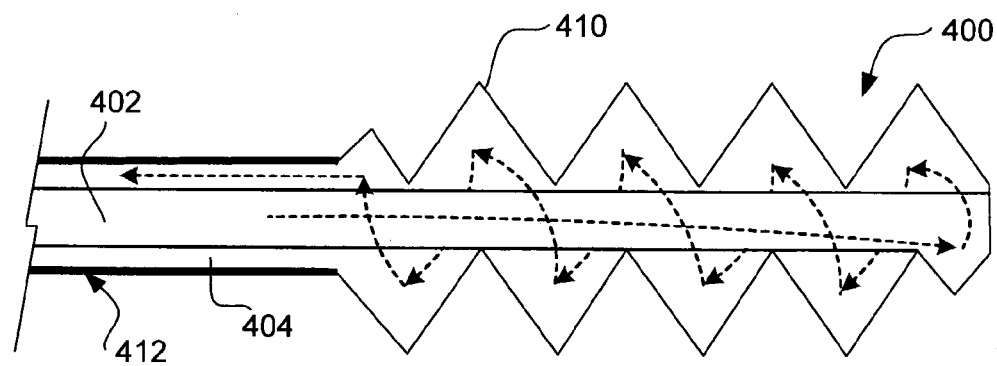
FIG. 26 is a partial cut-away view of an example embodiment of a catheter including an expandable member having a through-put passageway.

FIG. 24 shows another embodiment for achieving both fluid displacement and heat exchange with another inflatable member. Inflatable member 350 is shown disposed beyond the distal opening 362 of outer catheter 360. The inflatable member 350 is shown fully inflated and in fluid and mechanical communication with elongate tube 352. Elongate tube 352 and inflatable member 350 may include a single lumen for inflation into a closed chamber, but may in other embodiments resemble the dual lumen device including a flow-through inflatable member as shown in FIG. 26. The inflatable member 350 may be rotated to cause fluid displacement, or mere inflation of the member 350 may cause sufficient fluid displacement. Again, the inflatable member 350 may be inflated with a heating or cooling fluid, and adapted for inducing heat exchange between an inflation fluid and the surrounding fluid and tissue. Because inflatable member 350 is disposed outside outer catheter 360, it may in some embodiments be inflated to a greater diameter than if it were inside outer catheter 360, up to perhaps five or more millimeters.

Figure 25:
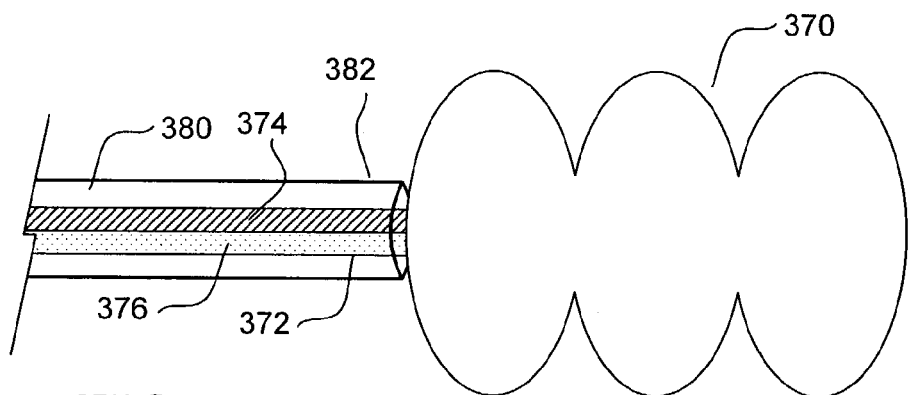
FIG. 25 is a partial side view of another example embodiment of a catheter including an expandable member disposed past the distal tip.

FIG. 25 shows another inflatable member disposed beyond the distal tip of a catheter. In the illustrative embodiment, a rounded inflatable member 370 is shown extending distal the opening 382 of catheter 380. A dual lumen fluid exchanging member 372 is shown in fluid communication with the inflatable member 370. The dual lumen fluid exchanging member 372 includes an inlet lumen 374 and an outlet lumen 376. Inlet lumen 374 may supply heated or cooled inflation fluid under pressure to inflatable member 370, while outlet lumen 376 can transport the inflation fluid away from inflatable member 370. The illustrative embodiment may improve the heat exchanging capabilities of the overall device by providing a continuous flow of controlled temperature fluid via inlet lumen 374. The inflation of inflatable member 370 can be caused by controlling the pressure of fluid within inflatable member 370, inlet lumen 374 and outlet lumen 376. Further, repeated inflation and deflation may cause sufficient displacement of surrounding CSF and tissue to induce both heat exchange and CSF flow. Again, the length and diameter of the inflatable member may be up to perhaps five or more millimeters in diameter and up to perhaps fifty or more millimeters in length. One advantage for the illustrative embodiments shown in FIGS. 24 and 25 is that a relatively large inflatable member may be introduced into the subarachnoid space without requiring a particularly large lumen catheter to perform the introduction, since the inflatable member may be inserted and advanced in an deflated state.

For example, with reference to FIG. 25, inflatable member 370 may be maintained in a deflated state inside the distal end of catheter 380 prior to insertion. After insertion of the distal end of catheter 380 into the subarachnoid space and advancement to a desired location inside the subarachnoid or intracranial spaces, the outer portion of catheter 380 may be retracted to expose inflatable member 370 or, alternatively, the inflation lumen 372 may be slidably disposed inside catheter 380 so that, once at the desired location, the inflation lumen 372 may be advanced, pushing inflatable member 370 past the distal tip of catheter 380. Then, repeated inflation and deflation of the inflatable member 370 may be used to induce fluid displacement and heat exchange inside the accessed area. Also, inflation of the inflatable member 370 and reciprocation of the inflation lumen 372 to move inflatable member 370 back and forth or forward and backward may be used to cause fluid displacement. A third method for causing fluid displacement could include providing the inflatable member 370 as an off-center device on the end of inflation lumen 372, so that rotation of the inflation lumen 372 would cause fluid displacement. Also, shaping the inflatable member 370 as an oblong shape could enable rotation to cause fluid displacement.

FIG. 26 shows an alternative construction for an inflatable member, such as those shown in FIGS. 23–25. While inflatable members may be filled and drained using a single inflation lumen, the inflatable member of FIG. 26 is not so constructed. Catheter 400 is shown as a coaxial catheter having an inner lumen 402 and an outer lumen 404. Other embodiments may use other dual lumen structures, for example, a side-by-side arrangement. The distal tip of catheter 400 is comprised of an inflatable member 410. As shown by the arrows inside both inner lumen 402 and outer lumen 404, an inflation fluid may pass under pressure through the inflatable member 410. For example, fluid may enter inflatable member 410 through inner lumen 404 and exit through outer lumen 402, although in alternative embodiments the fluid may flow in the opposite direction. The fluid may, for example, be passed out of the catheter entirely to a heat exchanger and pump (not shown), where the temperature and pressure of the fluid flowing through the inflatable member 410 may be controlled. For the illustrative embodiment of FIG. 26, the inflatable member 410 continually receives freshly cooled or heated fluid during inflation. The inflatable member 410 may be rotated as an Archimedean screw to cause fluid displacement around it, or it may be held stationary and CSF forced to pass over it as illustrated, for example, in FIG. 27.

The illustrative embodiment of FIG. 26 also includes another feature included in several embodiments. Catheter 400 is adapted to traverse a distance from an entry location in the spinal subarachnoid space until it reaches a desired location in either the subarachnoid or intracranial spaces. In order for catheter 400 to perform its function, fluid flowing through the lumens 402, 404 should be of a different temperature than the surrounding CSF and other bodily fluids and tissue. Once the fluid reaches the distal end of catheter 400 at the inflatable member 410, the fluid must be able to perform a heat exchange function with the surrounding tissue and fluids. To assist in this process, the catheter 400 may be adapted so that the proximal portion 412 has a lower thermal conductivity (indicated by the thickened lines in the figure), while the catheter 400 also includes inflatable member 410 that has a higher thermal conductivity. The catheter 400 may include a transition area having a thermal conductivity that is between the high thermal conductivity of the inflatable member 410 and that of of the proximal portion 412. Though the different thermal resistances are indicated in the Figure by a thickened line, this does not require that the material itself be thicker or thinner at any given point; indeed, the thermal conductivity may be varied by varying the material composition, conditions of fabrication, thickness, or any other factor that can affect thermal conductivity.

Figures 27A, 27B:
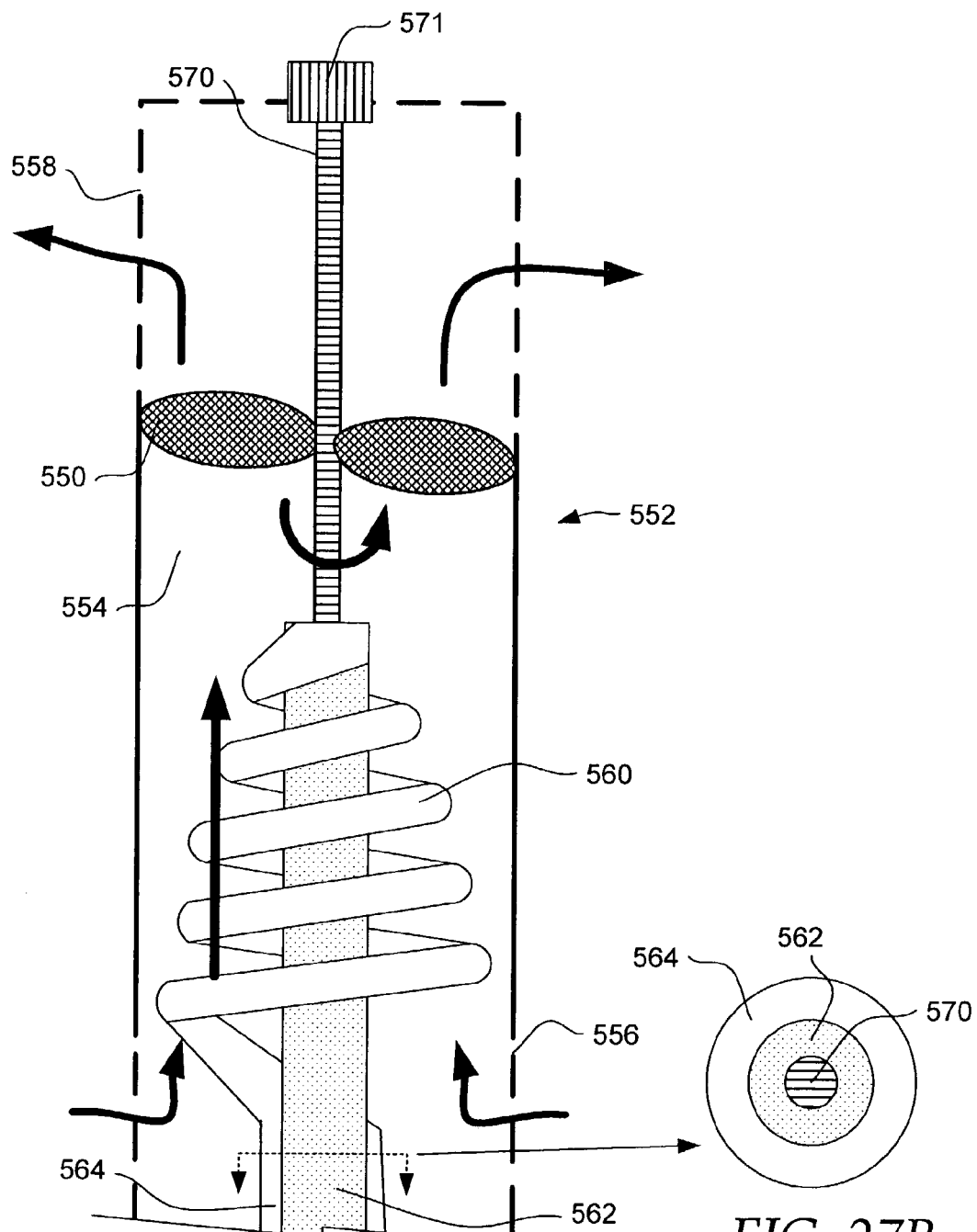
FIG. 27A is a partial side view of an example embodiment of a device including a fluid displacement apparatus and a heat exchange apparatus disposed inside a catheter.
FIG. 27B is a cross sectional view of a portion of the device of FIG. 27A.

FIG. 27 illustrates an example of an embodiment using a propeller 550 to move fluid within a catheter 552 including a lumen 554 and a heat exchanging member 560. The heat exchanging member 560 may be a rigid member, or may be a collapsible or inflatable member. The heat exchanging member 560 may be adapted for a heat exchanging fluid to be passed therethrough, to have a heat exchanging fluid inflate it, or may be constructed of a thermally conductive material such that a proximal portion of the heat exchanging member may be heated or cooled and the thermally conductive properties of the heat exchanging member may cause heat conduction from one location to another. For example, the heat exchanging fluid can be supplied to the heat exchange member 560 through a lumen in the inner catheter body 562 and be removed from the heat exchange member 560 through a lumen in the outer catheter body 564. As shown, the heat exchanging member 560 may be disposed in a spiraling shape, causing fluid that is displaced past it to come into contact along several locations.

The propeller 550 can be rotated by twisting drive wire 570, which may terminate at the distal end in a securing apparatus 572. The securing apparatus 572 may stabilize the distal end of wire 570, may include a direction selective ratchet, or may be placed to prevent the distal end of wire 570 from contacting tissue near the distal tip of catheter 552. The propeller 550 is adapted so that turning the drive wire 570 causes rotation of the propeller 550, which in turn causes displacement of fluid within the lumen 554 from a location of a proximal port 556 towards a distal port 558, the propeller 550 and heat exchanging member 560 being disposed between the ports 556, 558. Although ports 556, 558 are shown as perforated sections of catheter 552, they may also comprise single or multiple openings in catheter 552.

Figure 28A:
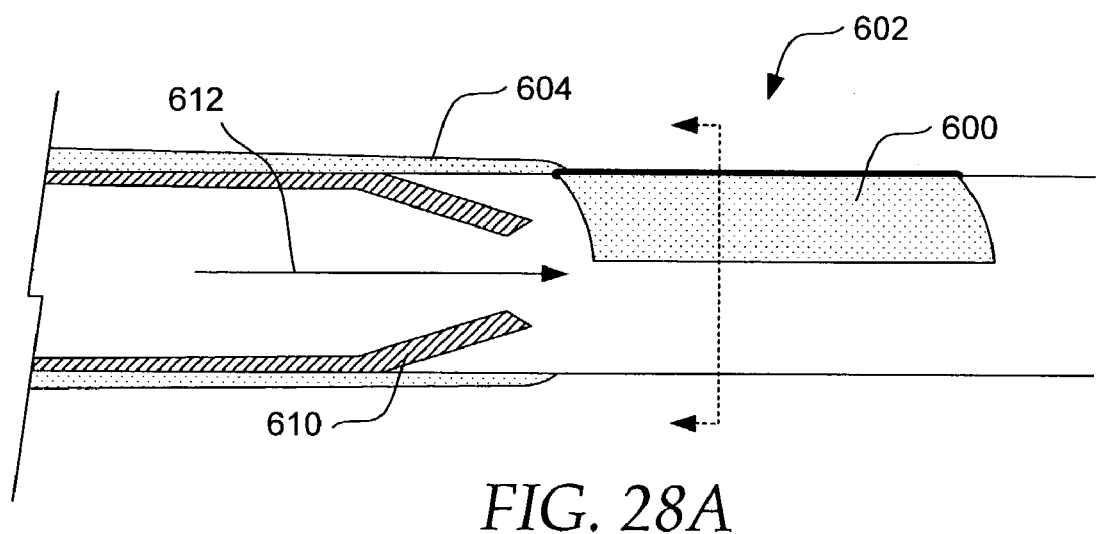
FIGS. 28A and 28C are partial side views of an example embodiment of a catheter including a shape memory member in a first shape and a second shape.
Figure 28B:
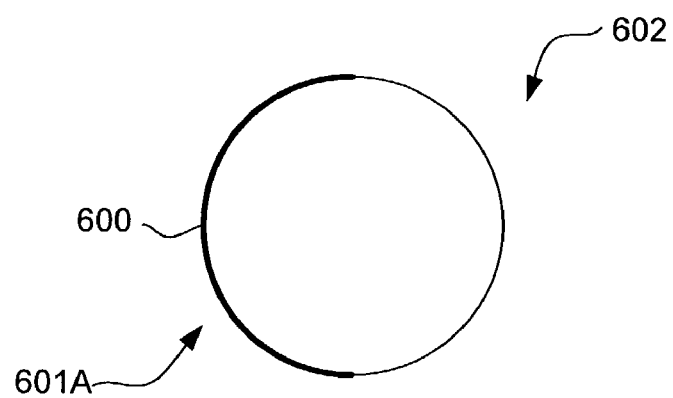
FIGS. 28B and 28D are cross sectional views corresponding to the shape memory members in the first shape and second shape as in FIGS. 28A and 28C.
Figure 28C:
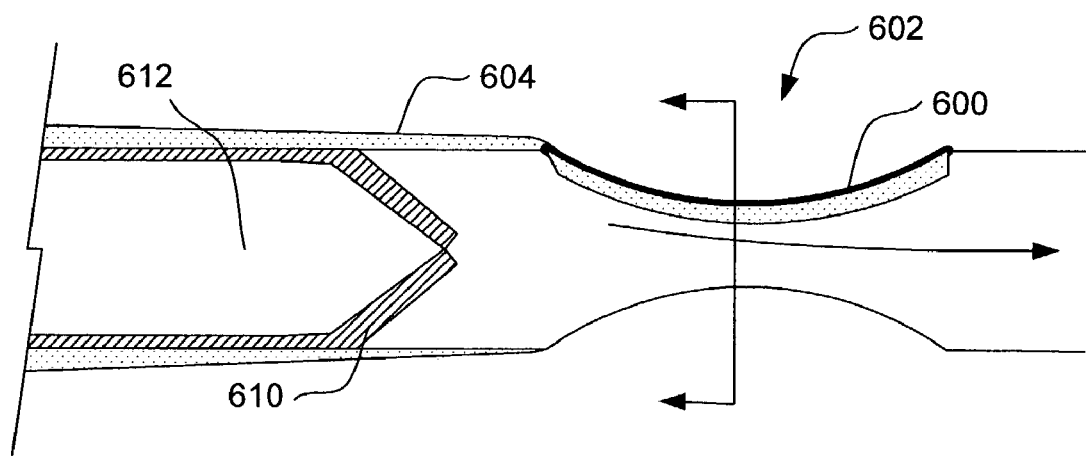
Figure 28D:
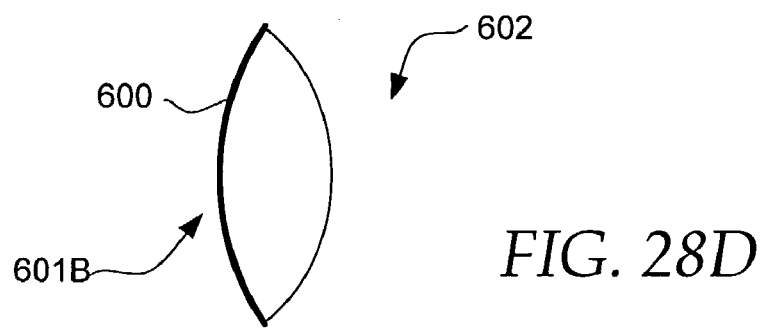

FIGS. 28A–E illustrate another embodiment, this time using a shape-memory material to provide actuation for fluid displacement. In several embodiments, the fluid referred to in relation to FIGS. 28A–E is CSF, but in at least some embodiments, other fluids may be treated with these methods. A shape memory member 600 is disposed in a section of a catheter 602. The shape memory member 600 includes fluid vessels therethrough, in fluid communication with an outer lumen 604 of the catheter 602. When fluid of a first temperature passes through the outer lumen 604 and into the shape memory member 600, the shape memory member 600 can assume a first shape 601A causing the catheter 602 in the area corresponding to the shape memory member 600 to assume a generally circular cross section, as shown in FIG. 28B. When a fluid of a second temperature passes through outer lumen 604 and into shape memory member 600, the shape memory member 600 assumes a second shape 601B causing the catheter 602 in the area corresponding to the shape memory member 600 to assume a more elongated cross section, as shown in FIGS. 28C and 28D. In other embodiments, the temperature of the shape memory material could be changed using other means, for example, the use of electrical resistance, or the like. For example, for an embodiment that heats an internal area, leads could run along, through, embedded within or otherwise from a proximal location to a location adjacent the shape memory material, with a resistive element placed between the leads adjacent the shape memory material, so that electrical current passed through the leads could cause the resistor to create heat and change the shape of the shape memory material.

With the shape memory member in the first shape 601A, the portion of the catheter 602 corresponding to the shape memory member 600 can contain a greater volume than when the shape memory member 600 assumes the second shape 601B. The actuation as described pushes fluid out of the area of the catheter 602 corresponding to the shape memory member 600. Valving apparatus 610 prevents fluid from flowing back (to the right), as shown in FIG. 28C, but allows fluid to flow forward (to the left) as shown in FIG. 28A. Thus, the combination of valving apparatus 610 and actuation provided by shape memory member 600 causes fluid to flow through the catheter 602 in the direction indicated by arrows 612, 613. A second valve apparatus may be provided on the other side of the shape memory member 600 to further control fluid flow and increase "pumping" efficiency.

Figure 28E:
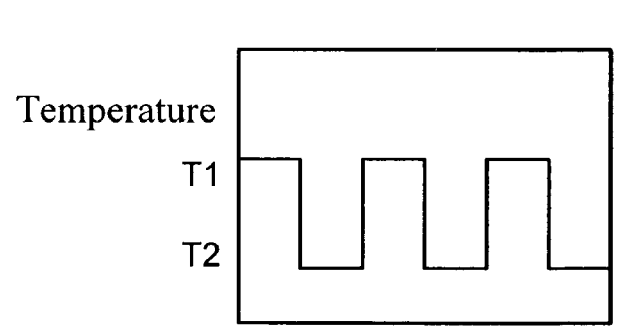
FIG. 28E is a diagrammatic representation of temperature variations with time for a fluid infused into the shape memory device of FIGS. 28A–D.

FIG. 28E illustrates a temperature versus time sequence that could be applied to cause pumping action with the apparatus illustrated in FIGS. 28A–D. The changing applied temperature may be used to cause actuation as described and continual pumping. Alternatively, rather than pumping fluid of a first temperature and a second temperature through vessels within the shape memory member 600, the shape memory member could be adapted to allow heat transfer with the pumped fluid. Thus, for example, the shape memory member 600 could assume the first shape 601A when at a temperature corresponding to the surrounding temperature of the pumped fluid, and could be switched to the second shape 601B by infusion of a fluid via lumen 604. As heat exchange with the pumped fluid causes the temperature of the shape memory member 600 to return to a temperature corresponding to the surrounding temperature of the pumped fluid, the shape memory member 600 would then return to the first shape 601A.

Figure 29A:
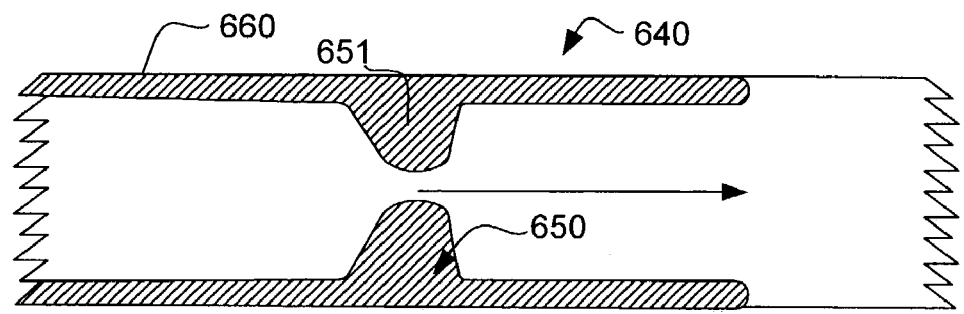
FIGS. 29A–C are partial side views of an example embodiment of a catheter including an inflatable member and a design and method for using the inflatable member to cause directional fluid displacement and heat exchange.
Figure 29B:
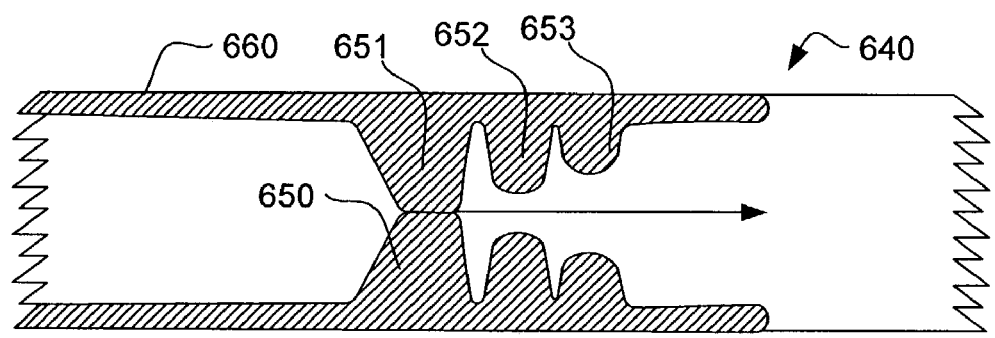
Figure 29C:
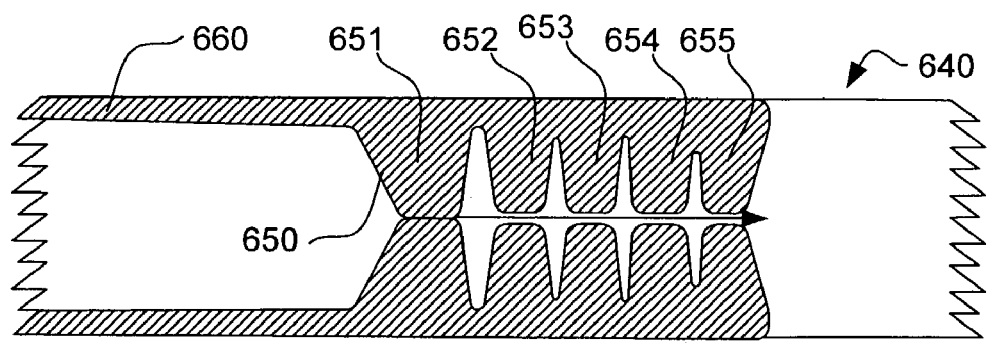

FIGS. 29A–C illustrate another embodiment using a catheter 640 including an inflatable member 650 to cause fluid displacement. The inflatable member 650 includes segments 651, 652, 653, 654, 655 that inflate in sequence from proximal to distal when pressure is applied to the inflatable member via inflation lumen 660. The most proximal first segment 651 inflates first, as shown in FIGS. 29A and 29B. Once fully inflated the first segment 651 blocks fluid from flowing from the distal side of the first segment 651 to the proximal side of the first segment 651. As the other segments of the balloon then inflate in order, 652 through 655, fluid is forced out of the area of the catheter 640 corresponding to the inflatable member 650. Because the fluid cannot flow past first segment 651, it must flow distally along the catheter 640. Again, the inflatable member 650 may be adapted to enable heat exchange between the pumped fluid and the fluid used to inflate the inflatable member 650.

Figure 30A:
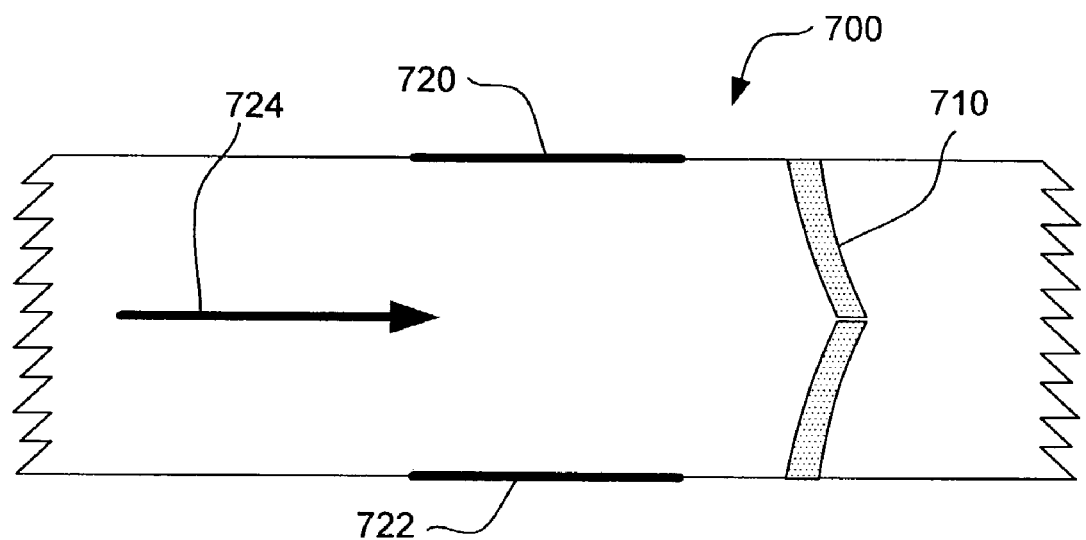
FIGS. 30A–B are partial side views of an example embodiment of a catheter including electrodes for causing actuation and a valving device for controlling flow direction.
Figure 30B:
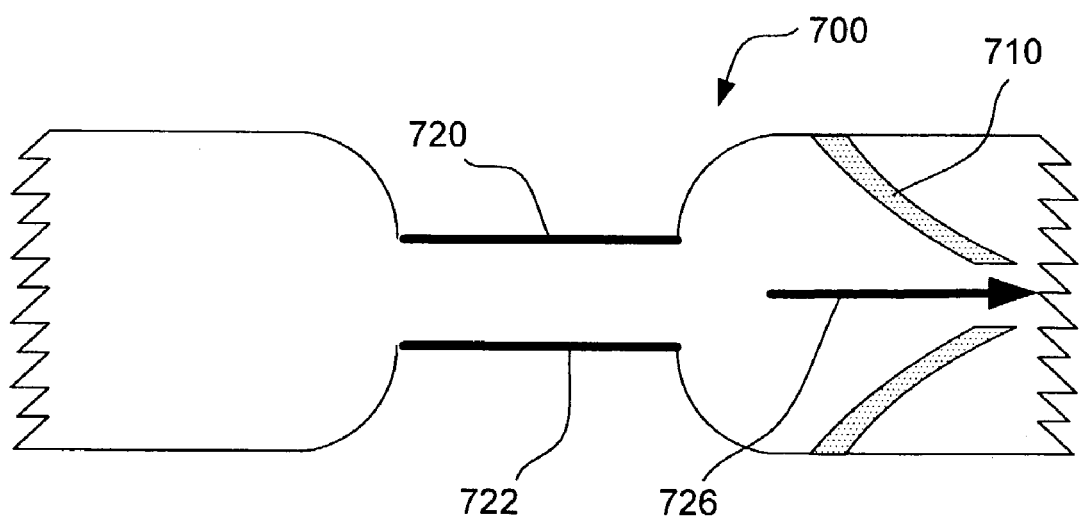

FIGS. 30A–B illustrate another embodiment. The illustrative embodiment of FIGS. 30A–B uses a catheter 700 having a valving apparatus 710. Electrodes 720, 722 are engaged with the walls of the catheter 700. Each electrode 720, 722 may be electrically connected via a wire (not shown) either integral to or disposed within catheter 700 to a source for electrostatic energy. Opposing polarities may be applied to the electrodes 720, 722 to create an attractive force between them, causing the catheter 700 walls to be impinged as shown in FIG. 30B. Alternatively, like polarities may be applied to the electrodes 720, 722 to cause the catheter walls to repel from one another as shown in FIG. 30A. Between the actuation supplied by the electrodes 720, 722 and the valve function supplied by the valving apparatus, fluid is pumped through the catheter 700, as shown with arrows 724, 726.

The embodiment of FIGS. 30A–B may be used with a separate heat exchanging apparatus, for example, as shown in FIGS. 23A–C. Electrostatic or magnetostatic force may be used in conjunction with the electrodes. Also, one or the other of the movements shown in FIGS. 30A–B can be assisted or performed entirely due to tension of the catheter, for example, the catheter may have elastic properties or may be rigid to oppose the movement caused by the forces supplied by the electrodes. In the case of use within an MR scanning machine, it may be possible to use the applied magnetic fields of the MR scanner to create actuation. However, it is also necessary when considering materials for use in the electrodes (as well as all devices and components described herein) to consider the likely effects of placing such materials inside the large magnetic fields used by some modern imaging equipment.

The above described embodiments illustrate different features of the overall invention, and may be used in conjunction with other structures or methods to provide heat exchange and fluid displacement as described without departing from the spirit. Further, the above features may be separated and combined in different configurations as well.

Monitoring Physiologic and Biochemical Properties

Figure 14:
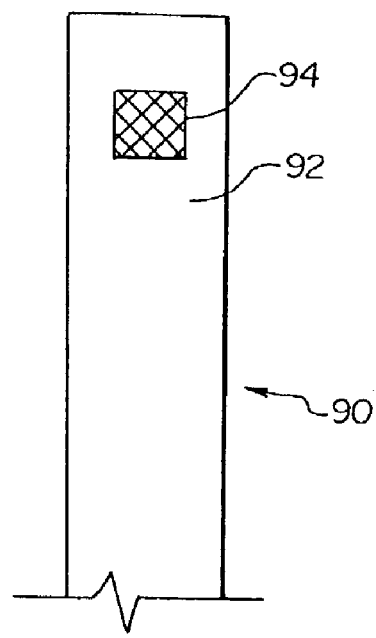
FIG. 14 is a partial side view illustrating a detector attached to the outside surface of a medical device.

Another use for the present invention includes placement of sensors or detectors at internal locations, for example, in the subarachnoid or intracranial spaces. In this regard, FIG. 14 illustrates an illustrative example including device 90 having wall 92 and detector 94 attached to wall 92. Detector 94, although shown as attached to the exterior of wall 92, may be embedded within wall 92 or beneath the outer surface of wall 92 in certain embodiments, depending, for example, on the depth of detector 94 below the outer surface and the type of material from which wall 92 is made. Further, wall 92 may have an opening, and detector 94 may be attached to the inside surface of wall 92 and extend across that opening, provided proper precautions are taken to avoid damaging detector 94 as device 90 is navigated. Additionally, the location of detector 94 may be varied, from being at an end of device 90, to being located at any position along wall 92.

Detector 94 may be an electroencephalography electrode useful for monitoring electrical activity. Detector 94 may be a sensor useful for monitoring a biochemical property such as pH, glucose concentration, oxygen tension, carbon dioxide concentration, or sodium concentration. Thus, one of those biochemical properties may be monitored using the sensor. Detector 94 may be a thermal sensor useful for monitoring temperature. Thus, temperature, such as of a fluid or tissue, may be monitored using the thermal sensor. Detector 94 may also be useful for monitoring neurotransmitter concentration. Also, detector 94 may be a pressure sensor, or may be capable of detecting properties of the CSF such as infusion and concentrations of impurities, drugs, antibiotics, or blood cells, for example. In some embodiments, the detector 94 may be disposed on a catheter, inserted and removed with the catheter, while in other embodiments, the detector 94 may be an implantable medical device that is placed by use of a catheter advanced through the spinal subarachnoid space to a desired location.

Figure 15:
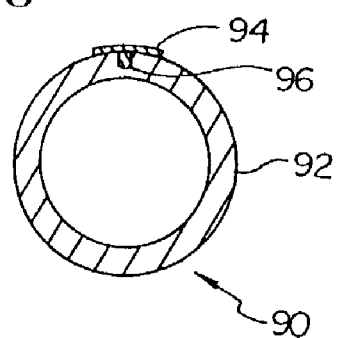
FIG. 15 is a cross-sectional view showing the detector depicted in FIG. 14 being coupled to a communication device illustrated as a wire positioned in the wall of the medical device.

FIG. 15 is a cross sectional view of device 90, showing that detector 94 may be coupled to a communication device that is illustrated as wire 96 embedded within wall 92. The communication device may travel along the length of device 90 any sufficient distance, and may exit, or extend away from, wall 92 at any suitable location, including prior to the end of device 90, at a hub coupled (whether permanently or otherwise) to the end of device 90, at the end of device 90, or at a valve apparatus (such as valve apparatus 36 illustrated in FIG. 3) coupled to the end of device 90. The communication device can then be linked to a station that processes the signal from the detector. The station may be configured to record data that it collects and/or generates in monitoring and/or controlling the detected attribute. The communication device can also take the form of a wireless communication using, for example, radio waves or other electromagnetic means of transmission. For example, wire 96 may be coupled to detector 94 to allow the wire to be used as an antennae, with detector 94 providing a signal output.

Figure 16:
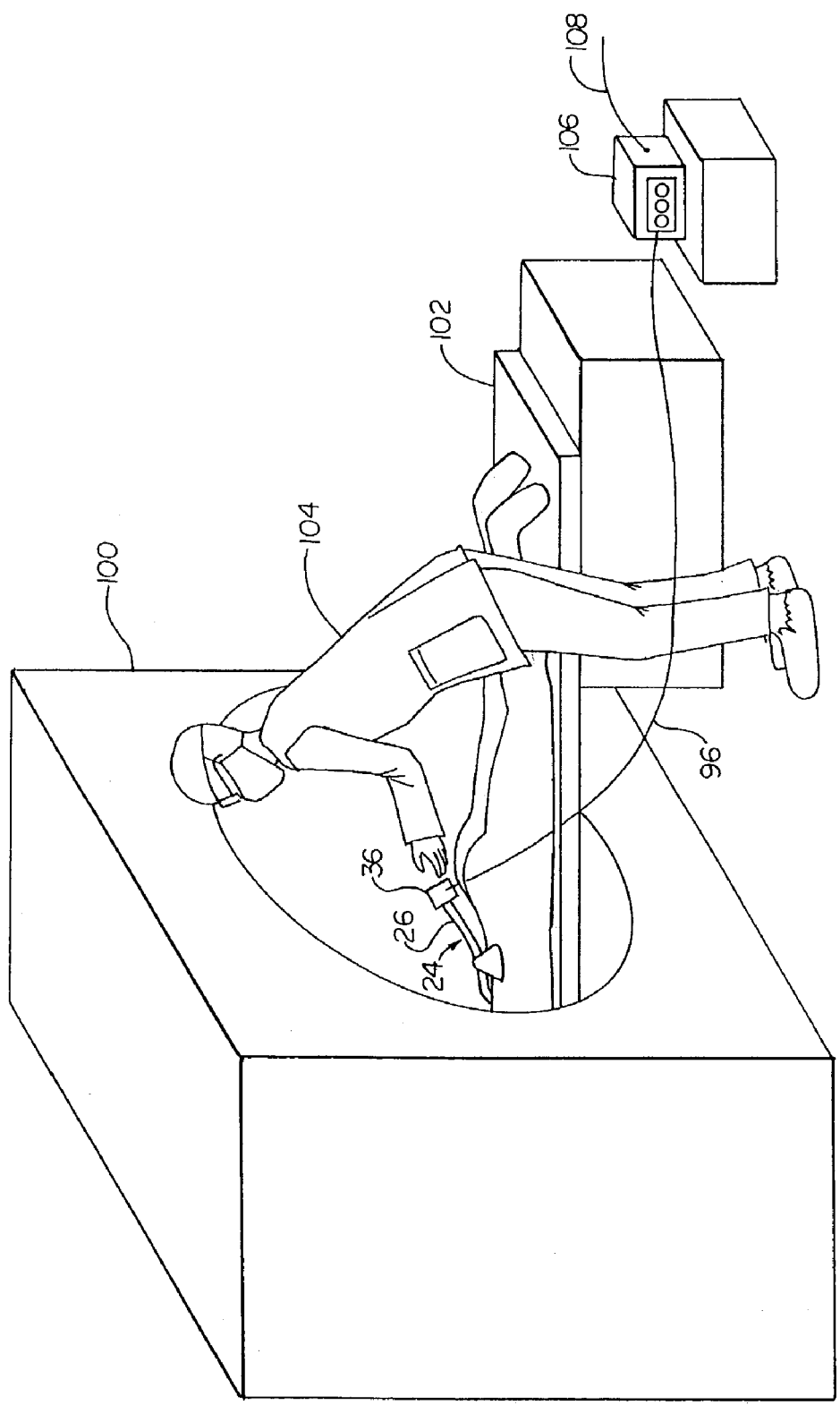
FIG. 16 illustrates an operator applying an example of the present methods to a patient positioned within an MR scanner.

FIG. 16 illustrates a patient positioned in MR scanner 100 and on top of sliding table 102. Operator 104 is positioned remotely from the target area being scanned such that the magnets within MR scanner 100 do not interfere with his or her manipulations. Sheath 24 is shown as being inserted into the patient, and a communication device illustrated as wire 96 is shown traveling from outside of valve apparatus 36 to station 106. Wire 96 is coupled to a detector (not shown) attached to the wall of the elongated member 24. Station 106 may be configured to record data that it collects and/or generates in monitoring and/or controlling the detected attribute on any suitable media, including paper and electronic data. Also, a second communication device in the form of wire 108 is illustrated as exiting station 106 and traveling to an undisclosed area where another operator can view the data generated and collected by station 106.

Figure 17:
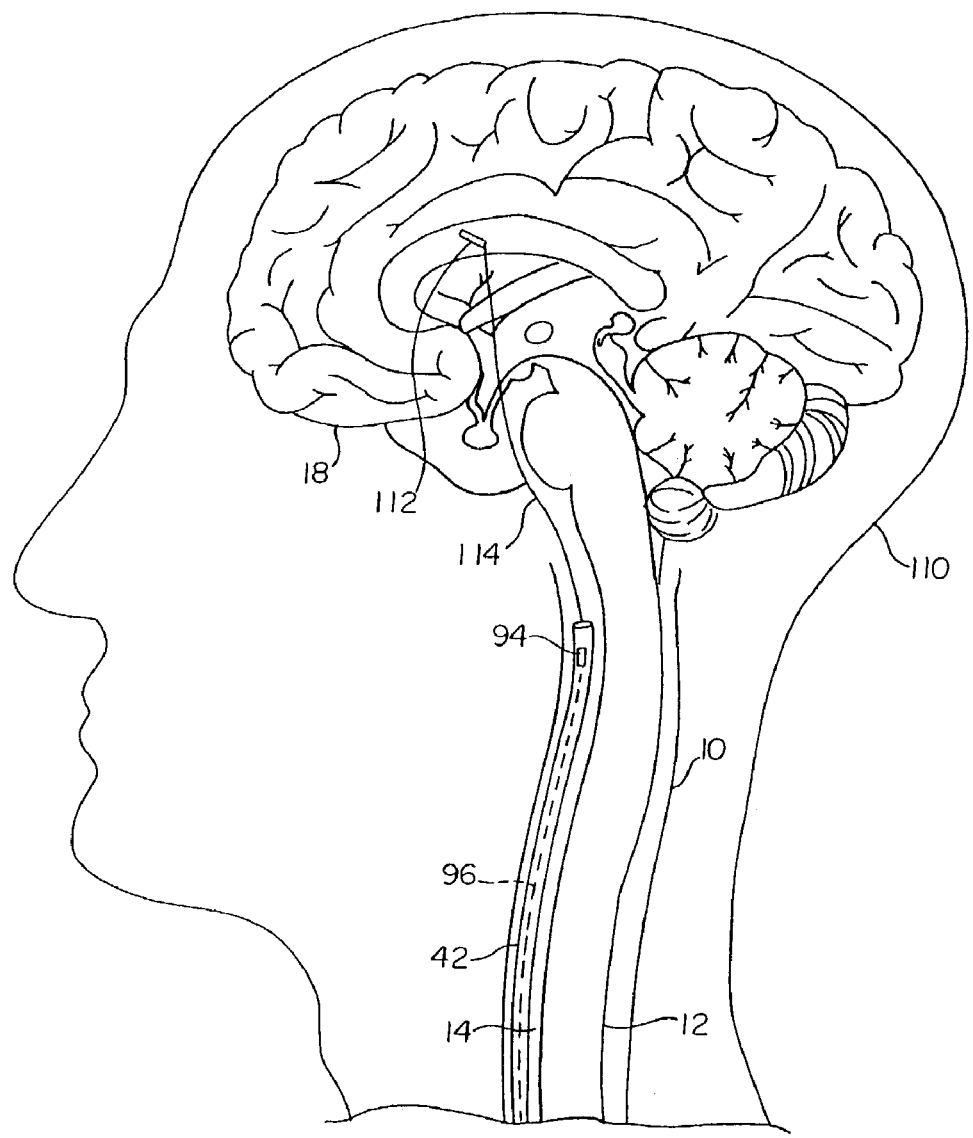
FIG. 17 illustrates a detector being placed in brain tissue.

The same types of monitoring that may be achieved using a detector attached to a device such as sheath 24 or catheter 42 (which is illustrated in the form of device 90 in FIG. 14), may also be achieved using a detector or detectors implanted in brain tissue or in the subarachnoid space. FIG. 17 illustrates detector 112 that is positioned intracranially. FIG. 17 shows brain 18 inside of head 110, and further shows that catheter 42 may have a wall in which detector 94 is located. FIG. 17 also illustrates that a communication device in the form of wire 96 is coupled to detector 94 and embedded within the wall of catheter 42, as indicated by the dashed lines. A detector delivery mechanism illustrated as wire 114 is shown as being coupled to detector 112. This coupling may be achieved electromagnetically or mechanically, for example. Detector 112 may be coupled to wire 114 in a way that will allow the detector to be detached from wire 114 once detector 112 has reached its intended destination. In such an embodiment, detector 112 may wirelessly communicate with a station like station 106 illustrated in FIG. 16. Alternatively, the detector delivery mechanism illustrated as wire 114 may remain coupled to detector 112 and serve as a communication device between detector 112 and a remote station. Detector 112 may include an anchoring mechanism for retaining its position once delivered. This includes an anchoring mechanism that deploys once detector 112 exits catheter 42; such an anchoring mechanism may have a non-tubular configuration. For example, one suitable anchoring mechanism that is also used in vascular systems involves "hooks" or "barbs" located at the tips of wire members of devices, which hooks engage the walls of vessels to hold the device in place. Such hooks may also be used as an anchoring mechanism to engage the dura in instances in which detector 112 is implanted in the subarachnoid space. Another suitable anchoring mechanism would be a flared end on detector 112, resembling conventional flared configurations on the tips of conventional ventricular shunt catheters. Such an anchoring mechanism would be useful in instances in which a detector 112 is placed either in brain tissue or in a catheter destined for a ventricle.

In addition to the embodiments illustrated in FIGS. 14, 15, and 17, multiple detectors 94 may be attached to the inside or outside surfaces of the wall of one of the present devices (such as sheath 24 or catheter 42), or placed within the wall of one of the present devices, in order to better monitor the various attributes discussed above. Furthermore, a single communication device (such as wire 96) may be used to link multiple detectors to a station. Additionally, each of the sub-elongated members illustrated in FIG. 13 may be provided with the detectors discussed above, in the manners discussed above. For example, both of the sub-elongated members shown in FIG. 13 may have walls that have detectors attached to them, and the lengths of those sub-elongated members may be such that the detector attached to one sub-elongated member may be placed in brain tissue and may be useful for monitoring oxygen tension, while the detector attached to the other sub-elongated member may be placed in cerebrospinal fluid and may be useful for monitoring sodium concentration.

Another form of monitoring the physiologic or biochemical conditions of tissue and/or fluids within the body includes what may be termed "microdialysis." This may include the withdrawal and analysis of small amounts of liquids such as extracellular fluid and/or CSF which may be encountered in the subarachnoid space as well as areas accessible via navigation of the subarachnoid space. For example, the CSF adjacent the brain may be accessed and sampled in a microdialysis procedure using the above noted methods of accessing the subarachnoid space. Intraspinal navigation may enable image-guided (for example X-ray or MRI guided) placement of catheters within the brain parenchyma as well as the rest of the subarachnoid space for purposes of monitoring extracellular fluid chemistry or pharcological agent levels. Some of the catheters discussed herein may be used for such monitoring and/or sampling, either via methods discussed herein or by other methods which may later be developed. Further, the methods discussed herein may be used to aid in such monitoring and/or sampling, either using catheters disclosed herein or by the use of other catheter-like devices that may enable fluid withdrawal or which may include apparatuses or mechanisms for facilitating such sampling and monitoring.

In some embodiments, fluids obtained via accessing the subarachnoid space and intracranial space may be tested for biochemical properties in conjunction with other activities. For example, while performing the function of exchanging or cooling CSF of a patient to effect localized cooling of tissue in the subarachnoid space, some of the CSF or another fluid may be sampled for purposes of testing biochemistry of the fluid.

Placement of Electroencephalography Electrodes

As discussed above, detectors that are electroencephalography (EEG) electrodes may be introduced into the subarachnoid space in both the spinal and intracranial regions, and in brain tissue using the present methods. By way of explanation, in epilepsy treatment, it is often difficult to localize the site of a seizure focus. One technique used in particularly difficult cases involves placement of EEG electrodes either directly on the surface of the brain (electrocorticography) or within the brain substance (depth electrode implantation). Since EEG monitoring involves detection of extremely weak electrical signals that are emitted from brain cells, elimination of interference from scalp muscles, elimination of signal resistance from the skull bone, and placement of electrodes closer to the brain tissue emitting those signals is one way to increase the sensitivity and specificity of localization and detection.

While increasing the sensitivity and specificity of epileptiform activity detection, such techniques as electrocorticography and depth electrode implantation have traditionally been invasive, using either burr holes in the skull for depth electrode placement or craniotomy for cortical array placement in electrocorticography. If bilateral monitoring is desired, bilateral burr holes or craniotomies have been used. However, using the present methods, EEG electrodes may be placed on the surface of the brain or within brain tissue via percutaneous entry into the spinal subarachnoid space and advancement superiorly into the intracranial space.

In instances in which EEG electrodes take the form of detectors 112 discussed above with respect to FIG. 17, multiple detectors may be linked with a single communication device that takes the form of a wire. Multiple wire and detector(s) combinations may be placed during a single procedure, and the different wires may have different diameters, different stiffnesses, or the like. Thus, arrays of EEG electrodes may be placed on or within brain tissue to map out the electroencephalogram from the deep brain structures. For example, a catheter having two passageways may be advanced to a desired location over a guidewire positioned in one of the two passageways. An EEG electrode may then be placed in a desired location through the open passageway. After placement, the catheter may be withdrawn over the guidewire, leaving the guidewire and the first EEG electrode in place. The catheter may then be reintroduced over the guidewire, and a second electrode placed in a desired location through the once-again open second passageway. This process may be repeated as many times as necessary. For another illustrative embodiment, a catheter may be introduced over a guidewire, and a second device, for example a wire having a detachable EEG electrode disposed near the distal tip of the wire, may be advanced into the catheter to the distal end, and the EEG electrode released; without removing the catheter entirely, additional EEG electrodes may be inserted in this fashion.

Spinal and Cerebral Stimulation

There are situations in medicine and in research where it is desirable to deliver an electrical impulse to the brain and spinal cord. Using the present methods, an electrode suited to such stimulation may be placed, thereby enabling the application of electric current, heat, or cryothermal stimulation of a patient's tissue. A transmission device such as a wire may be coupled to the electrode to introduce the stimulating signal to the electrode. The stimulating signal may also be introduced to the electrode via a wireless transmission. Furthermore, in certain embodiments in which a transmission device such as a wire is used, the wire may be linked to a station useful in delivering the stimulating signal, and that is located outside of the patient's body or implanted within the patient, such as a station that is implanted in the subcutaneous space of the patient. The methods and devices discussed above for inserting detectors may be used to place stimulation devices, also.

Implantation of Radioactive Pellets, or Beads, for Treatment of Tumors

The present methods can be used to implant radioactive pellets, or beads, into patients, in areas such as the brain, in order to irradiate a tumor. While the use of radioactive pellets for tumor irradiation is known, the placement of such pellets using the present methods is novel. As with all the other applications that may be achieved using the present methods, the placement of radioactive pellets may be monitored under direct MR visualization.

Ablation of Brain Lesions

In functional neurosurgery, it is sometimes desirable to create lesions in the brain. This is seen in chronic pain syndromes, Parkinson's disease, and other settings. Current techniques for creation of these lesions involve CT- or MR-guided stereotaxis, in which a cryothermal or thermal ablation device is introduced to the desired location in the brain via a burr hole in the skull that the neurosurgeon drills in the operating room.

Using the present methods, a device (such as sheath 24 or catheter 42) or a guidewire (such as guidewire 44) may be introduced into the subarachnoid space (for example, the spinal subarachnoid space) and advanced as described above with respect to FIG. 1 to a desired location. Energy, such as thermal energy or cryothermal energy, may then be applied either to an ablation device imbedded in or attached to the catheter, sheath, or guidewire or to an ablation device introduced through the passageway of the catheter or sheath such that a lesion is created in the adjacent tissue, such as brain tissue. Other areas of application include tumors that may be in locations that are either inaccessible via conventional techniques, or that require unacceptable morbidity to approach them via conventional techniques. Such locations may include locations in the brain stem, the spinal cord, the subarachnoid space, or the intracranial space. In cases in which the ablation device is attached to or embedded within a device or a guidewire, the ablation device may be positioned at the end of the device or guidewire, or it may be positioned at any suitable location along the length of the device or guidewire. In other embodiments, the ablation device may include a rotating member or a cutting member. Suction may be applied through a catheter or sheath lumen to retrieve cut-away tissue portions.

Using one or more imaging modalities to monitor the therapy resulting from the ablation may make it feasible to create a lesion, observe partial success, and enlarge the lesion without repositioning the introducing device (such as catheter 42), or with minimal manipulation of the introducing device. Furthermore, tissue ablation achieved using the present methods may be performed in conjunction with conventional surgery such that lesions are created either before or after conventional resections, either to enhance the resection preoperatively or to improve margins of incompletely-resected lesions, or to provide an alternate approach to large-scale resections in diseases with multiple brain lesions such as metastatic disease from different forms of malignancy.

Accessing One or More Ventricles

In medicine, the ventricular system is frequently catheterized, both temporarily (ventriculostomy) and permanently (shunting). This occurs to combat hydrocephalus, to monitor pressure and, less often, for introduction of various medications or withdrawal of cerebrospinal fluid. However, the current neurosurgical approach requires placement of a burr hole in the skull bone and insertion of the catheter through the brain tissue, usually the frontal or parietal lobe, to access the ventricles. Using the present methods of percutaneous subarachnoid navigation, the lateral ventricles, the 3rd ventricle, and the 4th ventricle may be accessed. Accordingly, using the present methods, at least one ventricle located within the head may be accessed. Imaging modalities may be used as described above (and with all the movements of medical devices described herein) to monitor the position of such devices as they approach and enter a ventricle.

Furthermore, using the present methods, at least one ventricle located within the head may be drained. For example, in applications involving shunting, there will be a need for placement of a shunt component in the peritoneal cavity or venous return to the heart. This may be accomplished using the present methods. For example, after percutaneously introducing a device into the spinal subarachnoid space at an entry location and advancing the device within the subarachnoid space, one or more ventricles located within the head may be accessed and/or drained. The draining may also be achieved using a mechanism that spans a ventricle and a drainage location, and that acts as a one-way valve that allows that CSF and other fluid to flow in one direction—away from the ventricle or ventricles in question. In another embodiment, the present methods are used to insert an implantable device for providing CSF drainage, pressure control, or equilibration from one area of the brain to another in order to, for example, treat hydrocephalus.

Brain Biopsies

The brain is a very soft and gelatinous tissue once the membrane surrounding it (pia) is penetrated. Neurosurgeons resecting brain often use a tubular apparatus attached to suction to aspirate brain tissue rather than cutting it with a scalpel or scissors. That quality of brain tissue should lend it to biopsy by way of aspiration.

Using the present methods, a device may be introduced through the passageway of a device that may be used to remove a part of the brain. For example, the device that may be used to remove a part of the brain may be a traditional stereotactic device that is configured for introduction through the passageway of a device such as a catheter.

Alternatively, a device may be coupled to suction by way of a syringe or other mechanism, and used to retrieve a sample of tissue located at the tip of the catheter or sheath. Another feature of biopsies is that often multiple samplings of tissue are required to retrieve diagnostic material. Hence, it may be necessary to reposition the catheter for more than one biopsy sample. Once the device has been positioned the first time, it is desirable to avoid having to repeat the navigation that was performed to achieve initial positioning. For example, a catheter may be positioned proximate a target area, and suction may be applied to a lumen in the catheter to retrieve a portion of the brain. The sheath or catheter may then be removed along a guidewire used to initially facilitate placement (leaving the guidewire in position), and if the tissue sample is inadequate, the catheter can be repositioned over the guidewire and another biopsy sample can be obtained in a similar manner.

As noted, for some embodiments, suction will be the only force used to withdraw brain tissue. In other embodiments, a rotating member may be used to cut tissue and pull it into a catheter. Some embodiments can use other cutting apparatus as well, for example, a reciprocating blade could be controlled from the proximal end of a catheter having the blade at the distal end of the catheter.

Treating Neurologic Conditions

Using the present methods, genetic material may be introduced through the passageway of a catheter and placed within a patient suffering from a neurologic condition in order to assist in treating that neurologic condition. Such genetic material may include human stem cells. Furthermore, neurologic conditions arising from pressure on cranial nerves may also be treated using the present methods. For example, the present methods may be used to perform microvascular decompressions. In such an application, a catheter having a lumen may be percutaneously introduced into the spinal subarachnoid space at an entry location; the catheter may be advanced within the subarachnoid space; and a device may be introduced through the lumen and placed between a vascular loop and one or more cranial nerves in order to relieve compression of the cranial nerve by the vascular loop. In another embodiment, a device may be introduced to cut a nerve to alleviate a neurologic condition.

Vascular Coagulation or Cauterization

In conventional surgery, a metallic electrode is applied to a bleeding vessel and a current is applied through the electrode that heats the tissue such that the vessel is cauterized. That cauterization is achieved with a "two-point" apparatus via approximation of the points of a forceps, thus completing the current loop. Using the present methods, vessels may be coagulated at the time of surgery, either because they are observed to bleed or in order to prevent bleeding. For example, a catheter may be percutaneously introduced into the spinal subarachnoid space at an entry location and advanced via the subarachnoid space, and an apparatus such as a "two-point" or "Bovie" apparatus (which are used in conventional surgery or neurosurgery) may be connected near the distal end of the catheter, or the catheter may include a lumen and the apparatus may be advanced through the lumen. Monopolar cauterization is also known, and could be performed in much the same manner as above in other embodiments.

Thus an apparatus having a cauterization element and a transmission device (such as a wire, an insulated wire, a wire loop, or an insulated wire loop) connected to the cauterization element that is configured for attachment to a current-inducing apparatus may be used with the present methods to apply heat to a vessel, thereby cauterizing or coagulating it. Alternatively, the apparatus may include a set of forceps positioned at the end of a guidewire as the cauterization element, which forceps would function to open and close and act similarly to the forceps on conventional "two-point" devices. The transmission device may be attached to one of the present devices, including a guidewire. In other embodiments, the strong magnetic fields used to perform MR scanning could be used by a small cauterizing device, the cauterizing device being adapted so that a changing magnetic field induces a cauterizing current in the device. The transmission device that is part of this apparatus may be a wire loop that flares slightly after it exits the passageway through which it is introduced.

Notes on Methodology for Catheters

The above apparatuses can be introduced to a desired location in several ways. Some methods being by percutaneously introducing a sheath for introducing devices into the spinal subarachnoid space; those methods including the sheath continue by passing other devices through the sheath. A next step can be to introduce a guidewire or a guide catheter. The guidewire may be passed through the sheath if included, and advanced into the spinal subarachnoid space for some distance until it reaches a desired location. In some embodiments MR imaging or other imaging modalities can be used to monitor the progress of the guidewire. Once the guidewire is in place, a guide catheter may be introduced. The guide catheter includes a lumen, which may be either a short lumen or may extend for a substantial distance through the catheter, for receiving the guidewire. The guide catheter can follow the guidewire using the lumen. In some embodiments, the guidewire is advanced completely to its desired location before introducing the guide catheter, while in other embodiments the guidewire may be advanced a short distance, the guide catheter advanced so the distal end of the guide catheter is near the distal tip of the guidewire, and the steps repeated until both the guidewire and the guide catheter reach the desired location.

In embodiments including the guide catheter, an apparatus catheter carrying a desired apparatus, such as one of those explained above, can be advanced to a desired location by passing through a lumen in the guide catheter. The guide catheter could be included to protect or contain the apparatus catheter until it reaches the desired location. The guide catheter may also be used to shield surrounding tissue and membranes from irritation or damage caused by passage of multiple apparatus catheters in instances where multiple apparatus catheters may need to be introduced.

In other embodiments, the guide catheter may be omitted, and an apparatus catheter may be introduced over the guidewire. Again, the apparatus catheter may be introduced once the guidewire reaches the desired location, or it may be introduced in a more incremental fashion as the guidewire is pushed forward a distance, and the apparatus catheter follows shortly thereafter. One reason for the incremental advance of the apparatus catheter may be to enhance the pushability of the guidewire by providing a reinforcement for a distance inside the subarachnoid space. Another reason for the incremental advance may be that the guidewire may not be well suited for pushing against the membranes inside the subarachnoid space, for example, when the pia mater must be pierced, there is a possibility of bowing of the guidewire that could damage tissue in the spinal subarachnoid space.

Other embodiments may not include a guidewire. Such embodiments may use a catheter that may be passed through a sheath if included and advanced into the spinal subarachnoid space in similar fashion to that of the guidewire. For such embodiments, the catheter used may be a guide catheter through which apparatus catheters may be introduced, or the first catheter inserted may also be the apparatus catheter itself.

Cadaver Studies

Materials and Methods

Two recently deceased, unembalmed male human cadavers were placed in prone positions. Using fluoroscopic guidance, lumbar punctures were performed in each subject at both the L3–4 and L4–5 interspaces using a standard, single-wall puncture angiography needle. A 0.038 inch guidewire was then introduced and directed superiorly. Subsequently, a 5 French (F) angiographic dilator was advanced into the subarachnoid space over the guidewire to dilate the tract, and a 5F arterial sheath was placed with its tip directed superiorly. In each cadaver, one sheath was subsequently used for catheterization posterior to the spinal cord and the other was used for catheterization anterior to the spinal cord.

Following sheath placement, angiographic techniques were applied to the subarachnoid space. Specifically, under fluoroscopic guidance a hydrophilic-coated angle-tipped guidewire (Radifocus Glidewire, Terumo, Inc., Tokyo, Japan, distributed by Meditech Boston Scientific Corp., Watertown, Mass.) was advanced with its tip directed either anteriorly or posteriorly under operator control. Care was taken to maintain a midline position whenever possible, but it could not always be maintained. The advancement was performed with inflation of the subarachnoid space via saline infusion. The pressure of the infusion was easily controlled via management of the height of the flush bag above the patient's spine, though the pressures of the infusion and of the subarachnoid space were not specifically monitored.

After entering the cranial space, manipulations with the catheters were undertaken to explore areas for catheterization. Following catheterization manipulations, the catheters were left in place for subsequent dissection. The sheaths were cut at the skin with the introducers and microcatheters in place using standard wire cutters. The stumps of the systems were then oversewn and the cadavers were embalmed.

Following embalming, one cadaver was examined for evidence of spinal cord injury from the catheterization process. Laminectomy was performed throughout the cervical and thoracic spine and extended inferiorly to the point of catheter entry. The opened dura was photographed with the catheters in place. The spinal cord was removed and photographed with the ventral catheter in place. Brain dissections were performed to confirm catheter locations and to examine for unanticipated injury to brain tissue, with specific attention to the optic chiasm region in the case of catheters which passed through that region.

Results

In each case, the guidewire advanced relatively easily through the thoracic and cervical spine. In some cases, the catheter was advanced readily without guidewire placement. Once at the foramen magnum, attempts were made with the posterior catheters to enter the 4th ventricle. Observation was made during these attempts that navigation of the retrocerebellar space in the posterior fossa occurred relatively easily, on some occasions circum-navigating the posterior fossa to a position anterior to the pons. Also, advancement superiorly behind the cerebellum to the level of the tentorium occurred relatively easily. In each cadaver, a tough membrane was encountered at the base of the skull when midline catheterization was attempted. Whereas deflection of the guidewire for lateral or posterior catheterization occurred easily, the soft tip of the guidewire was inadequate for penetration of the membrane in the midline and the stiff end of the guidewire was used to penetrate the membrane. Subsequently, catheterization superiorly proceeded easily. In Cadaver 1, the posterior fossa catheter ultimately traversed the cerebellum during an attempt at fluoroscopically-directed 4th ventricular catheterization. In Cadaver 2, the 4th ventricle was successfully catheterized and injected with contrast, as described below.

Attempts were made without complete success to determine the location of the 4th ventricle using only fluoroscopy. Contrast injections resulted in intracranial spilling of contrast without outline of cerebellar structures. Blind passes with the catheter to where the 4th ventricle should be resulted in successful catheterization of the 4th ventricle in one of the two subjects. This was confirmed with contrast injection showing filling of the 4th ventricle, retrograde flow into the aqueduct of Sylvius, flow into the 3rd ventricle, and subsequent flow into the frontal horns of the lateral ventricles bilaterally via the foramina of Munro.

In both subjects, catheterization of the subarachnoid space anterior to the pons occurred, easily. Catheters as large as 5F were successfully advanced to this position. At the upper pontine level, a tough membrane was encountered in both subjects that would not permit higher catheterization using standard techniques. In both cases, the guidewire was deflected repeatedly from that location, regardless of multiple catheter repositioning attempts. Therefore, the guidewire was reversed and the stiff end of the guidewire was used to "punch" through this membrane. The membrane was believed to be the membrane of Lilequist, though this could not be confirmed with certainty subsequent to the dissection. Once it was crossed, catheterization to the suprasellar cistern with the standard end of the microguidewire (Radifocus™ Guide Wire M, Terumo, Inc., Tokyo, Japan, Tapered Glidewire Gold™ 0.018–0.013 inches, distributed by Target Therapeutics Boston Scientific Corp., Fremont, Calif.) proceeded smoothly. A Transit® 18 microcatheter (Cordis® Endovascular Systems, Johnson & Johnson, Miami Lakes, Fla.) was used in most cases, using in some cases a Tracker™ 38 catheter (Target Therapeutics® Boston Scientific Corp., Fremont, Calif.) as a guide catheter. In Cadaver 1, a single 4F introducer catheter was used that came from a company bought by Medtronics (MIS, Inc., Sunnyvale, Calif.) that is now no longer commercially available. With that catheter, the introducer catheter was advanced to the suprasellar cistern.

Once in the suprasellar cistern in Cadaver 1, advancement of the catheter was relatively easy, and catheterization of the sylvian fissure was observed and confirmed when contrast was injected and seen to flow dependently within the fissure. The catheter was left in that position and the subject was embalmed.

In Cadaver 2, catheterization of the suprasellar cistern was followed by experimentation regarding the degree of control had over placement. First, the frontal fossa on the side opposite from the previously catheterized middle fossa was catheterized. The catheter was advanced along the orbital roof and observed to curve superiorly, with its tip ultimately anterior to the frontal lobe and deep to the frontal sinus. The catheter was then withdrawn to the location on the orbital roof and this was confirmed with contrast injection. Next, that catheter was repositioned and the contralateral floor of the middle cranial fossa was catheterized and confirmed with contrast injection.

The posterior fossa catheter was then advanced and seen to be in the 4th ventricle, as described above. After contrast injection, some opacification of the 3rd ventricle was seen. This opacification was used as a "road map" for the anteriorly placed catheter and attempts were made to catheterize the 3rd ventricle directly through the region of the interpeduncular cistern (with fluoroscopy, the exact position was not identified). The pial lining of the undersurface of the brain resisted perforation with the soft end of the guidewire and the ventricle was elevated by the attempt but not punctured. Ultimately, however, the 3rd ventricle was entered successfully, as evidenced by drainage of the retained contrast. This was subsequently confirmed directly by contrast injection through the 3rd ventricular catheter. This subject was then embalmed.

Cadaver 1 was the only subject in which the spinal component of the catheterization was examined anatomically. Following full spinal laminectomy from the upper cervical area to the area of puncture in the lumbar spine, the posterior dura was incised and reflected. The dorsal introducer catheter was seen lying superficial to the spinal cord without apparent spinal cord violation or laceration. This was then removed and the spinal cord was resected by cutting the nerve roots bilaterally and lifting it out, retaining the ventral catheter with the spinal cord. It was observed to traverse anterolaterally, weaving anterior and posterior to different nerve roots. Again, there was no apparent spinal cord violation or laceration.

In Cadaver 1, anatomic exposure of the brain was preceded by latex impregnation of the vasculature following decapitation, with arteries impregnated with red latex and veins impregnated with blue latex. Dissection was performed via extensive bone drilling of the left frontotemporal area to reproduce an expanded surgical approach to the sylvian fissure and the region of the basilar apex. Exposure using an operating microscope revealed the microcather anterior to the midbrain, between the clivus and midbrain. It was followed inferiorly as it migrated to the right side of the basis pontis. There was no apparent violation of cerebral structures by the catheter during its passage anterior to the brain stem. The catheter traversed laterally in a sulcus in the left sylvian fissure. Removal of the temporal lobe revealed the catheter in the sylvian fissure, near branches of the middle cerebral artery. The posterior fossa catheter was observed to enter the cerebellum and was not pursued via further detailed dissection.

Dissection of Cadaver 2 revealed the 3rd ventricular catheter to be in place as suspected from the radiographs, located within the 3rd ventricle. The catheter was seen passing anterior to the brain stem along the clivus without brain stem penetration. Also, the basilar artery was seen separate from the catheter. The point of penetration of the 3rd ventricle was essentially vertical in the midline from the interpeduncular cistern. The 4th ventricular catheter was under some tension and sprang laterally as the cerebellum was split in the midline and its exact location could not be reconstructed. However, based on the images during contrast injection, it appeared to lie in the cerebellar tissue in the roof of the 4th ventricle.

Those skilled in the art will recognize that the present invention may be manifested in a variety of forms other than the specific embodiments described and contemplated herein. Accordingly, departures in form and detail may be made without departing from the scope and spirit as described in the appended claims.

What is claimed is:

1. A method of treating the CSF in a subarachnoid space of a vertebrate organism, the method comprising:
    providing a catheter having a proximal end, a distal end, and an elongate shaft extending therebetween, the catheter coupled to a device having the capacity for moving a fluid;
    percutaneously introducing the catheter with the device into the subarachnoid space at an entry location corresponding to a spinal portion of the subarachnoid space;
    advancing the caterer within the sub arachnoid space so that the device is at least partially within the subarachnoid Space; and
    activating the device to treat the CSF within the subarachnoid space.

2. The method of claim 1, wherein treating the CSF includes creating flow of CSF, and the step of activating the device results in creation of a flow of CSF within the subarachnoid space.

3. The method of claim 2, wherein the device comprises an Archimedean screw engaged with an elongate shaft for turning the Archimedean screw.

4. The method of claim 3, wherein the Archimedean screw comprises a collapsible member.

5. The method of claim 4, further including the steps of:
    introducing the Archimedean screw into the spinal subarachnoid space in a collapsed state;
    advancing the Archimedean screw to a desired location;
    causing the Archimedean screw to convert from the collapsed state into an operational state; and
    rotating the Archimedean screw to cause movement of the CSF.

6. The method of claim 2, wherein the device includes a first electrode and a second electrode, and the method further includes the Step of inducing an electrostatic force between the first electrode and the second electrode to cause displacement of the fluid.

7. The method of claim 6, wherein the device further includes a flexible member, wherein the first electrode is fixed to the flexible member and the induced electrostatic force causes a change in shape of the flexible member.

8. The method of claim 7, wherein the flexible member is made of a shape memory material.

9. The method of claim 7, wherein the flexible member is disposed under tension.

10. The method of claim 2, wherein the elongate shaft includes a lumen, and the step of activating the device causes the CSF to pass through a distal portion of the lumen.

11. The method of claim 1, further including providing a heat exchanger adapted to perform a heat exchange with the CSF.

12. The method of claim 11, wherein the catheter includes a conduit enabling a heat-exchanging fluid to pass therethrough between a proximal location and the heat exchanger.

13. The method of claim 11, wherein the conduit includes a section disposed within the spinal subarachnoid space.

14. The method of claim 11, wherein the heat exchanger includes a balloon.

15. The method of claim 14, further comprising the steps of:
inflating the balloon with a heat exchanging fluid; and
deflating the balloon.

16. The method of claim 15, further including the step of repeating the steps of inflating the balloon with a heat exchanging fluid and deflating the balloon.

17. The method of claim 15, further including the steps of:
monitoring a cardiac cycle of the vertebrate organism; and
performing the step of inflating the balloon with a heat exchanging fluid at a time chosen to correspond to a portion of the cardiac cycle of the vertebrate organism.

18. The method of claim 15, further including the steps of:
monitoring a cardiac cycle of the vertebrate organism; and
performing the step of deflating the balloon at a time chosen to correspond to a portion of the cardiac cycle of the vertebrate organism.

19. The method of claim 11, wherein the device comprises a flexible member, the method further including:
passing a heat exchanging fluid to the device; and
causing the flexible member to change shape.

20. The method of claim 19, wherein the flexible member has shape memory properties such that, when disposed at the body temperature of the vertebrate organism, the flexible member assumes a first shape, and passing the heat exchanging fluid to the device causes the flexible member to assume a second shape.

21. The method of claim 1, wherein the device includes a flexible member, and wherein the step of activating the device includes the step of causing the flexible member to move.

22. The method of claim 21, wherein the step of causing the flexible member to move includes applying an electrostatic force.

23. The method of claim 21, wherein the step of causing the flexible member to move includes applying a magnetostatic force.

24. The method of claim 21, wherein the step of causing the flexible member to move includes applying an acoustic wave.

25. The method of claim 21, wherein the step of causing the flexible member to move includes the step of providing an ultrasonic signal.

26. The method of claim 1, wherein said treating involves reducing cellular metabolic rates in a portion of tissue of a patient; wherein the step of advancing the catheter includes advancing the catheter through the spinal subarachnoid space to location within either the spinal subarachnoid space or an adjacent intracranial subarachnoid space; wherein the catheter has an infusion port, and the step of treating includes providing a cooling fluid at a temperature below the patient's normal body temperature, and pumping the cooling fluid through the infusion port.

27. The method of claim 1, wherein said treating involves cooling tissue in a subarachnoid space of a vertebrate organism; wherein the step of providing a catheter includes providing a catheter including an elongate shaft having a proximal end, a distal end, a first lumen, a second lumen, and a heat exchanger disposed adjacent the distal end in fluid communication with the first lumen and the second lumen; wherein the step of advancing the catheter includes advancing the distal end of the catheter within the subarachnoid space and positioning the heat exchanger adjacent the tissue; wherein the step of activating the device includes providing a flow of cooling fluid through the first lumen to the heat exchanger and removing the cooling fluid from the heat exchanger through the second lumen.

28. The method of claim 1, wherein said treating involves cooling CSF in a subarachnoid space of the vertebrate organism, wherein the step of providing a catheter includes providing a catheter including an elongate shaft having a distal end, a proximal end, a first lumen having an output ports, and a second lumen having an intake port, wherein the output port is disposed distally of the input port; wherein the step of advancing the catheter includes advancing the distal end of the catheter at least ten centimeters within the suharachnoid space; wherein the step of treating includes removing CSF from the subarachnoid space through the intake port and the second lumen, cooling the removed CSF, and introducing the cooled CSF back into the subarachnoid space through the first lumen and the output port.

29. The method of claim 28, wherein the step of advancing the distal end of the catheter at least ten centimeters within the subarachnoid space is performed with the assistance of robotic means.

30. The method of claim 1 wherein the step of providing a catheter includes providing a catheter having a fluid moving apparatus for moving a fluid disposed proximate the distal end, and a heat exchanger for providing heat exchange with a fluid or tissue disposed proximate the distal end; wherein the step of activating the device includes activating the fluid moving apparatus and/or the heat exchanger.

31. The method of claim 30, wherein the heat exchanger includes a thermally conductive member, and the step of activating the heat exchanger involves flowing a heat exchanging fluid in thermal communication with the thermally conductive member.

32. The method of claim 30, wherein the heat exchanger is pan of the fluid moving apparatus.

33. The method of claim 30, wherein the fluid moving apparatus includes a collapsible member, wherein the step of activating the fluid moving apparatus includes creating movement of a fluid by causing the collapsible member to move from a collapsed state to a non-collapsed state.

34. The method of claim 33, wherein the heat exchanger includes the surface of the collapsible member.

35. The method of claim 30, wherein the fluid moving apparatus includes an inflatable member; wherein the step of activating the fluid moving apparatus includes creating fluid movement by inflating the inflatable member.

36. The method of claim 35, wherein the fluid movement is created by repeated inflation and deflation of the inflatable member.

37. The method of claim 36, wherein the fluid moving apparatus causes fluid flow within a lumen in the elongate shaft.

38. The method of claim 37, wherein the inflatable member includes two segments, a first segment proximate the second segment, the first segment adapted to inflate before the second segment, the inflation of the first segment providing a valving function controlling the direction of fluid flow through the lumen.

39. The method of claim 30, wherein the heat exchanger includes an inflatable member.

40. The method of claim 39, wherein the heat exchanger effects heat exchange by repeated inflation and deflation of the inflatable member.

41. The method of claim 40, wherein the heat exchanger effects heat exchange by passing a fluid through the inflatable member.

42. The method of claim 30, wherein the fluid moving apparatus includes a rotatable member adapted to cause fluid movement when rotated.

43. The method of claim 30, wherein the fluid moving apparatus includes a collapsible member that causes fluid movement when deployed from a collapsed position.

44. The method of claim 30, wherein the fluid moving apparatus includes a collapsible member that causes fluid movement when collapsed from a deployed position.

45. The method of claim 1, wherein the step of providing a catheter includes providing a catheter having a proximal end, a distal end, a fluid displacer disposed along a location between the proximal end and the distal end, and a pumping lumen extending from a location proximal the fluid displacer to a location distal the fluid displacer; wherein the step of activating the device includes activating the fluid displacer to cause a fluid to move within the pumping lumen.

46. The method of claim 45, wherein the fluid displacer comprises a propeller, and the step of activating the device includes activating the propeller.

47. The method of claim 46, wherein the propeller is attached to a rotation shaft; wherein the step of activating the propeller includes rotating the rotation shaft, causing the propeller to turn, causing fluid to move within the pumping lumen.

48. The method of claim 46, wherein the propeller comprises an inflatable member.

49. The method of claim 48, wherein the step of activating the propeller includes rotating the inflatable member once the inflatable member is at least partially inflated, thereby causing fluid displacement.

50. The method of claim 45, wherein the fluid displacer comprises an inflatable member.

51. The method of claim 50, wherein the step of activating the fluid displacer involves inflation of the inflatable member, thereby reducing the cross sectional area of the pumping lumen.

52. The method of claim 50, wherein the fluid displacer further includes a valve for providing flow selectivity in the pumping lumen.

53. The method at claim 45, wherein the fluid displacer is disposed near the distal end of the catheter.

54. The method of claim 45, wherein the catheter is adapted so that, during the step of advancing the catheter to a desired location within the body of a patient, the fluid displacer is located internally with respect to the patient.

55. The method of claim 45, wherein the fluid displacer includes a first electrode and a second electrode disposed on opposing sides of the pumping lumen.

56. The method of claim 55, wherein a portion of the pumping lumen adjacent the first electrode is flexible; wherein the method further comprises the step of applying a voltage to the first and second electrodes, thereby causing an electrostatic force between the first electrode and the second electrode, reducing the cross sectional area of the pumping lumen.

57. The method of claim 45, wherein the catheter further includes a heat exchanger for heating or cooling the fluid in the pumping lumen.

58. The method of claim 57, wherein the heat exchanger includes an inflatable member.

59. The method of claim 58, wherein the fluid displacer uses the inflatable member.

60. The method of claim 58, wherein the catheter further includes an inflation lumen in fluid communication with the inflatable member.

61. The method of claim 60, wherein the catheter further includes a deflation lumen in fluid communication with the inflatable member.

62. The method of claim 1, further including the step of advancing the catheter into an intracranial portion of the subarachnoid space.

* * * * *

UNITED STATES PATENT AND TRADEMARK OFFICE
CERTIFICATE OF CORRECTION

PATENT NO. : 7,150,737 B2
APPLICATION NO. : 10/328560
DATED : December 19, 2006
INVENTOR(S) : Phillip D. Purdy et al.

It is certified that error appears in the above-identified patent and that said Letters Patent is hereby corrected as shown below:

Column 11
Line 57, delete "hang-up", and insert therefor --hang up--.

Column 14
Line 25, delete "otbers", and insert therefor --others--.

Line 40, delete "refracted", and insert therefor --retracted--.

Column 36
Line 37, delete "caterer", and insert therefor --catheter--.

Line 37, delete "sub arachnoid", and insert therefor --subarachnoid--.

Line 39, delete "Space", and insert therefor --space--.

Line 61, delete "Step", and insert therefor --step--.

Column 37
Line 14, delete "11", and insert therefor --12--.

Column 38
Line 27, delete "suharachnoid", and insert therefor --subarachnoid--.

Line 36, delete "claim 1 wherein", and insert therefor --claim 1, wherein--.

Line 49, delete "pan", and insert therefor --part--.

Line 51, delete "member, wherein", and insert therefor --member; wherein--.

UNITED STATES PATENT AND TRADEMARK OFFICE
CERTIFICATE OF CORRECTION

PATENT NO. : 7,150,737 B2
APPLICATION NO. : 10/328560
DATED : December 19, 2006
INVENTOR(S) : Phillip D. Purdy et al.

It is certified that error appears in the above-identified patent and that said Letters Patent is hereby corrected as shown below:

Column 40

Line 10, delete "at", and insert therefor --of--.

Signed and Sealed this

Twentieth Day of March, 2007

JON W. DUDAS
*Director of the United States Patent and Trademark Office*